(12) United States Patent
Nguyen-Kim et al.

(10) Patent No.: US 8,039,568 B2
(45) Date of Patent: Oct. 18, 2011

(54) ANIONIC ETHYL METHACRYLATE COPOLYMERS AND USE THEREOF

(75) Inventors: Son Nguyen-Kim, Hemsbach (DE); Gabi Winter, Ludwigshafen (DE); Matthias Laubender, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 535 days.

(21) Appl. No.: 11/665,881

(22) PCT Filed: Oct. 19, 2005

(86) PCT No.: PCT/EP2005/011239
§ 371 (c)(1),
(2), (4) Date: Apr. 19, 2007

(87) PCT Pub. No.: WO2006/045508
PCT Pub. Date: May 4, 2006

(65) Prior Publication Data
US 2008/0286221 A1 Nov. 20, 2008

(30) Foreign Application Priority Data
Oct. 22, 2004 (DE) .......................... 10 2004 051 648

(51) Int. Cl.
*C08F 126/06* (2006.01)
(52) U.S. Cl. ..................... 526/258; 526/263; 526/303.1; 526/307; 526/307.6; 526/307.7; 526/317.1; 526/318.4; 526/319
(58) Field of Classification Search .................. 526/258, 526/263, 303.1, 307, 307.6, 307.7, 317.1, 526/318.4, 319
See application file for complete search history.

(56) References Cited

U.S. PATENT DOCUMENTS

| | | | |
|---|---|---|---|
| 3,405,084 A | 10/1968 | Bohac et al. | |
| 3,836,537 A | 9/1974 | Boerwinkle et al. | |
| 4,237,253 A | 12/1980 | Jacquet et al. | |
| 4,324,780 A | 4/1982 | Jacquet et al. | |
| 4,748,989 A | 6/1988 | Nuber et al. | |
| 4,767,613 A | 8/1988 | Nuber et al. | |
| 4,814,101 A | 3/1989 | Schieferstein et al. | |
| 5,110,582 A | 5/1992 | Hungerbuhler et al. | |
| 5,196,188 A | 3/1993 | Potthoff-Karl et al. | |
| 5,639,841 A * | 6/1997 | Jenkins .......................... | 526/333 |
| 5,643,581 A | 7/1997 | Mougin et al. | |
| 5,880,252 A | 3/1999 | Kim et al. | |
| 6,166,093 A | 12/2000 | Mougin et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,410,004 B1 | 6/2002 | Kim et al. | |
| 6,524,564 B1 * | 2/2003 | Kim et al. .................. | 424/70.12 |
| 6,800,276 B2 | 10/2004 | Kim et al. | |
| 7,015,294 B2 * | 3/2006 | Dausch et al. ................ | 526/319 |
| 7,063,834 B2 | 6/2006 | Mougin et al. | |

FOREIGN PATENT DOCUMENTS

| | | |
|---|---|---|
| CA | 2058017 A1 | 6/1992 |
| CA | 2203686 A1 | 11/1997 |
| CA | 2319930 A1 | 3/2001 |
| CA | 2507721 A1 | 3/2001 |
| DE | 2150557 | 6/1972 |
| DE | 2817369 A1 | 10/1978 |
| DE | 3227334 A1 | 1/1984 |
| DE | 3708451 A1 | 10/1988 |
| DE | 3929973 A1 | 3/1991 |
| DE | 4223006 A1 | 1/1994 |
| DE | 4223066 A1 | 1/1994 |
| DE | 4225045 A1 | 2/1994 |
| DE | 4333238 A1 | 4/1995 |
| DE | 19507249 A1 | 9/1996 |
| EP | 62002 A2 | 10/1982 |
| EP | 100890 A2 | 2/1984 |
| EP | 256458 A2 | 2/1988 |
| EP | 257444 A2 | 3/1988 |
| EP | 331994 A2 | 9/1989 |
| EP | 480280 A1 | 4/1992 |
| EP | 491629 A1 | 6/1992 |
| EP | 636361 A1 | 2/1995 |
| EP | 751162 A1 | 1/1997 |
| EP | 805169 A2 | 11/1997 |
| EP | 1035144 A1 | 9/2000 |
| EP | 1084696 A1 | 3/2001 |
| JP | 10-226988 | * 8/1998 |
| JP | 11-158231 | * 6/1999 |
| WO | WO-9725021 A1 | 7/1997 |
| WO | WO-9732917 A1 | 9/1997 |

OTHER PUBLICATIONS

Schrader K. H., "Fundamentals and Formulations of Cosmetics," Verlag Hüthig, 2nd edition, pp. 319-355.

* cited by examiner

*Primary Examiner* — Bernard Lipman
(74) *Attorney, Agent, or Firm* — Connolly Bove Lodge & Hutz LLP

(57) ABSTRACT

The present invention relates to copolymers which comprise ethyl methacrylate, at least one α,β-ethylenically unsaturated amide group-containing compound and at least one monoethylenically unsaturated carboxylic acid in copolymerized form, to cosmetic and pharmaceutical compositions which comprise at least one such copolymer, and to the use of these copolymers.

17 Claims, No Drawings

ANIONIC ETHYL METHACRYLATE COPOLYMERS AND USE THEREOF

RELATED APPLICATIONS

This application is a national stage application (under 35 U.S.C. §371) of PCT/EP2005/011239 filed Oct. 19, 2005, which claims the benefit of German application 10 2004 051 648.0 filed Oct. 22, 2004.

The present invention relates to copolymers which comprise ethyl methacrylate, at least one α,β-ethylenically unsaturated amide group-containing compound and at least one monoethylenically unsaturated carboxylic acid, to cosmetic and pharmaceutical compositions which comprise at least one such copolymer, and to the use of these copolymers.

PRIOR ART

Polymers with film-forming properties have found diverse uses in the pharmaceutical and cosmetics sector.

In pharmacy, they serve, for example, as coatings or binders for solid drug forms.

In cosmetics, polymers with film-forming properties are used inter alia for setting the hair, improving the structure of the hair and shaping the hair. They serve, for example, as conditioners for improving the dry and wet combability, the feel to the touch, the shine and the appearance, and impart antistatic properties to the hair. Requirements which are placed on film-forming polymers for use as setting resins are, for example, strong hold (even at high atmospheric humidity), high flexural rigidity and elasticity, ability to be washed out of the hair, compatibility in the formulation and a pleasant feel of the hair treated therewith. The provision of products with a complex profile of properties often presents difficulties. There is thus a need for film-forming polymers for hair cosmetic compositions which are able to form essentially smooth, tack-free films, in particular have a good setting action and at the same time impart to the hair good sensory properties, such as elasticity, a pleasant feel and volume.

In hairspray formulations, good propellant gas compatibility, suitability for use in low-VOC formulations (VOC=volatile organic compounds), good sprayability, good solubility in water or aqueous/alcoholic solvent mixtures and good ability to be washed out are also desired.

Copolymers based on (meth)acrylate which are water-soluble in alkaline conditions are often used in the field of cosmetics as hair-setting compositions.

EP-A 331 994 describes hair-setting preparations comprising copolymers of a) 40 to 60% by weight of $C_3$-$C_{12}$-alkyl methacrylates, b) 20-40% by weight of $C_4$-$C_{10}$-N-alkyl-substituted acrylamides and c) 10-25% by weight of (meth) acrylic acid. Preference is given to using copolymers of a) isobutyl methacrylate, b) N-tert-octylacrylamide and c) acrylic acid.

EP-A 491 629 describes an aerosol preparation comprising a neutralized tetrapolymer consisting of a) 4 to 6% by weight of acrylic acid, b) 42 to 52% by weight of N-vinyl-pyrrolidone, c) 15 to 25% by weight of N-tert-butylacrylamide and d) 20 to 26% by weight of ethyl methacrylate.

DE 2 817 369 describes copolymers in which at least three of the monomer units have a methacrylic acid structure, where the copolymers consist of 22 to 64 mol % of N,N-dimethylaminoethyl methacrylate, 13 to 72 mol % of methyl methacrylate, 6 to 23 mol % of methacrylic acid and 0 to 22 mol % of at least one N-substituted alkyl(meth)-acrylamide.

EP-A 62 002 describes terpolymers which are prepared by copolymerization of a) 40 to 60% by weight of a N-alkylacrylamide or N-alkylmethacrylamide having 1 to 4 carbon atoms in the alkyl moiety with b) 35 to 50% by weight of a $C_1$-$C_4$-hydroxyalkyl ester or preferably $C_1$-$C_4$-alkyl ester of acrylic acid or methacrylic acid and c) 3 to 11% by weight of an α,β-unsaturated monocarboxylic acid or dicarboxylic acid.

DE 32 27 334 describes copolymers obtained by free-radical copolymerization of 20 to 75 parts by weight of at least one $C_2$-$C_{20}$-alkyl ester of (meth)acrylic acid, 5 to 50 parts by weight of at least one nitrogen-containing, neutrally reacting water-soluble monomer, 1 to 25 parts by weight of at least one cationic group-containing monomer and 1 to 25 parts by weight of at least one olefinically unsaturated $C_3$-$C_5$-carboxylic acid copolymerizable with a), b) and c) which, measured in ethanol at 25° C., have a K value in accordance with Fikentscher of from 15 to 75.

DE 42 23 006 describes hair-treatment compositions which comprise, as film former, copolymers which are obtainable by copolymerization of (a) 30 to 80% by weight of an acrylic or methacrylic ester which in each case as homopolymer has a glass transition temperature of more than 20° C. or of mixtures of acrylic and methacrylic esters which produce copolymers with a glass transition temperature of more than 20° C. during the copolymerization, (b) 5 to 25% by weight of acrylic acid, methacrylic acid or mixtures thereof and (c) 10 to 45% by weight of N-vinylpyrrolidone, N-vinylcaprolactam or mixtures thereof in the presence of free-radical-forming polymerization initiators, and which, in the form of the free carboxylic acid groups, have K values (determined in accordance with H. Fikentscher in 1% strength by weight solution in ethanol at 25° C.) of from 10 to 80, wherein the copolymers are prepared by the process of precipitation polymerization.

EP-A 805 169 describes copolymers obtainable by free-radical polymerization of a mixture of
a) 30 to 72% by weight of t-butyl acrylate or t-butyl methacrylate or a mixture thereof,
b) 10 to 28% by weight of acrylic acid or methacrylic acid or a mixture thereof and
c) 0 to 60% by weight of at least one further free-radically copolymerizable monomer.

German patent application with the file reference 10357486.7, which was unpublished at the priority date of the present application, describes copolymers obtainable by free-radical polymerization of a monomer mixture comprising
a) tert-butyl acrylate and/or tert-butyl methacrylate,
b) at least one α,β-ethylenically unsaturated amide group-containing compound of the general formula

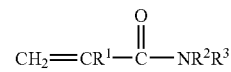

in which
$R^1$ is H or $C_1$-$C_4$-alkyl,
$R^2$ and $R^3$, independently of one another, are H or $C_1$-$C_4$-alkyl, or $R^2$ and $R^3$, together with the nitrogen atom to which they are bonded, can also be a 4- to 7-membered heterocycle,
with the proviso that the sum of the carbon atoms of radicals $R^1$, $R^2$ and $R^3$ is at most 4, and
c) acrylic acid.

EP-A 256 458 describes copolymers for use as hair fixatives obtained by free-radical polymerization of
a) 20 to 60% by weight of vinylpyrrolidone,
b) 20 to 60% by weight of an acrylamide mono- or dialkylated on the N atom and having 1 to 8 carbon atoms in the alkyl radical or their mixtures, c) 5 to 60% by weight of an alkyl or hydroxyalkyl ester of acrylic or methacrylic acid having 1 to 4 carbon atoms in the alkyl radical or 2 to 4 carbon atoms in the hydroxyalkyl radical or mixtures of these esters or 3 to 12% by weight of acrylic acid or methacrylic acid or 2 to 48% by weight of an alkyl or hydroxyalkyl ester of acrylic acid or methacrylic acid having 1 to 4 carbon atoms in the alkyl and 2 to 4 carbon atoms in the hydroxyalkyl radical or mixtures of these esters and 3 to 12% by weight of acrylic acid or methacrylic acid, where the % by weight are based on the total weight of the monomers, which is soluble in lower alcohols having 1 to 4 carbon atoms and has a K value of from 15 to 75.

Sticter environmental regulations and growing ecological awareness increasingly demand ever lower fractions of volatile organic components (VOC) in, for example, hairsprays.

According to the VOC guidelines (solvent guideline), VOCs are volatile organic compounds which, at 293.15 K, have a vapor pressure of 0.01 kPa or more and, under the particular use conditions, have a corresponding volatility.

The VOC content in hairsprays is essentially set by the nonaqueous solvents and the propellants. For this reason, instead of nonaqueous solvents, recourse is increasingly being made to water as solvent. This replacement of the organic solvents, however, is associated with problems, particularly in the field of hairspray formulations.

Thus, formulations of the abovementioned film-forming polymers from the prior art which satisfy the corresponding VOC regulations, are, for example, not sprayable or are sprayable only after further dilution and are thus only of limited suitability for use in hairsprays. This in turn leads to films which sometimes do not have the required mechanical quality and thus inadequate setting action and poor hold for the hair.

Requirements placed on hair-setting resins, are, for example, strong hold at high atmospheric humidity, elasticity, good ability to be washed out of the hair, compatibility in the formulation, greatest possible smoothness and low tack of the film formed and a pleasant feel of the hair treated therewith. In the case of spray formulations, a homogeneous distribution of small droplets for forming a fine spray pattern is also desired in particular. The provision of products with a complex profile of properties often presents difficulties.

An object of the invention was to provide polymers suitable for cosmetic low-VOC preparations which, upon use, lead to strong hold at high atmospheric humidity, good ability to be washed out of the hair, compatibility in the low-VOC formulation, good rheological properties, such as high flexural rigidity and elasticity, and greatest possible smoothness and low tack of the film formed and a pleasant feel of the hair treated therewith, and in the case of the use in a low-VOC spray preparation produce a good spray pattern.

This object is achieved through the provision of copolymers obtainable by free-radical polymerization of a monomer mixture M comprising
a) 50 to 80% by weight of ethyl methacrylate or 50 to 80% by weight of a mixture of ethyl methacrylate and at least one compound of the general formula I

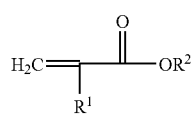

(I)

in which
$R^1$ is H or $CH_3$,
$R^2$ is $C_1$-$C_4$-alkyl,
b) 3 to 25% by weight of at least one α,β-ethylenically unsaturated amide group-containing compound of the general formula II

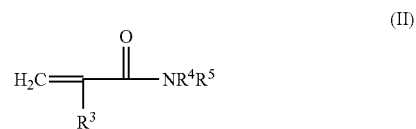

(II)

in which
$R^3$ is H or $C_1$-$C_4$-alkyl,
$R^4$ and $R^5$, independently of one another, are H or $C_1$-$C_4$-alkyl, or $R^4$ and $R^5$, together with the nitrogen atom to which they are bonded, may also be a 4- to 7-membered heterocycle,
with the proviso that the sum of the carbon atoms of the radicals $R^3$, $R^4$ and $R^5$ is at most 4,
c) 15 to 35% by weight of at least one monoethylenically unsaturated carboxylic acid,
d) 0 to 20% by weight if appropriate of further free-radically polymerizable monomers different from a), b) and c),
where the monomer mixture M comprises at least 20% by weight of ethyl methacrylate.

In the text below, compounds which can be derived from acrylic acid and methacrylic acid are sometimes referred to in short by adding the syllable "(meth)" to the compound derived from acrylic acid.

For the purposes of the present invention, water-soluble monomers and polymers are understood as meaning monomers and polymers which dissolve in water in an amount of at least 1 g/l at 20° C. Water-dispersible monomers and polymers are understood as meaning monomers and polymers which disintegrate into dispersible particles under the application of shear forces, for example by stirring. Hydrophilic monomers are preferably water-soluble or at least water-dispersible. The copolymers according to the invention are generally water-soluble.

The copolymers according to the invention are suitable in a particularly advantageous manner for use in cosmetic compositions, in particular in hair-treatment compositions. They serve preferably for producing elastic hairstyles coupled with strong hold. Advantageously, they are additionally characterized both by good propellant gas compatibility, and also good solubility in water or aqueous/alcoholic solvent mixtures. They can thus be formulated either to give hairsprays with high contents of propellant gas (VOC at least 85% by weight) or to give formulations with low VOC values (generally not more than 55% by weight, based on the total weight of the composition). In any case, the hairspray formulations are characterized by very good sprayability and ability to be washed out of the hair.

Component a)

Component a) is ethyl methacrylate or a mixture of ethyl methacrylate and at least one further monomer chosen from the group consisting of methyl(meth)acrylate, ethyl acrylate, methyl ethacrylate, n-propyl(meth)acrylate, isopropyl(meth)acrylate, n-propyl ethacrylate, ethyl ethacrylate, isopropyl ethacrylate, n-butyl(meth)acrylate, n-butyl ethacrylate, tert-butyl(meth)acrylate, tert-butyl ethacrylate, isobutyl(meth)acrylate, isobutyl ethacrylate, sec-butyl(meth)acrylate, butyl ethacrylate.

The copolymers according to the invention comprise, based on the total weight of the monomers used for the polymerization at least 50% by weight, preferably at least 55% by weight, particularly preferably at least 60% by weight and at most 80% by weight, preferably at most 75% by weight and in particular at most 70% by weight, of component a) in copolymerized form.

As component a), preference is given to ethyl methacrylate.

If ethyl methacrylate is present in a mixture with further (meth)acrylates as component a), then the fraction of ethyl methacrylate in the monomer mixture M of all monomers to be polymerized is at least 20% by weight.

Component b)

As component b), the copolymers comprise at least one amide of an $\alpha,\beta$-ethylenically unsaturated monocarboxylic acid of the general formula I in copolymerized form. Preferably, in the compounds of the general formula I, the radicals $R^2$ and $R^3$ are both H, or one of the radicals is $R^2$ and $R^3$ is H and the other is $C_1$-$C_4$-alkyl.

Preferably, the amides of the general formula I are derived from acrylic acid, methacrylic acid or ethacrylic acid as $\alpha,\beta$-ethylenically unsaturated monocarboxylic acid. Preferably, component b) is chosen from acrylamide, methacrylamide, N-methyl(meth)acrylamide, N-ethyl(meth)acrylamide, N-propyl(meth)acrylamide, N-isopropyl(meth)acrylamide, N-(n-butyl)acrylamide, N-(sec-butyl)acrylamide, N-(tert-butyl)acrylamide, N,N-dimethyl(meth)acrylamide, N,N-diethylacrylamide, N-acryloyl-morpholine, N-acryloylpiperazine, N-(meth)acryloylpyrrolidine and mixtures thereof.

Preferably, component b) corresponds to the general formula II where $R^4$ is H and $R^5$ is H or $C_1$-$C_4$-alkyl. Accordingly, preference is given to those components b) of the general formula II whose nitrogen atom carries at least one hydrogen atom.

Component b) is preferably chosen from the group consisting of acrylamide, methacrylamide, N-methyl(meth)acrylamide, N-ethyl(meth)acrylamide, N-n-propyl(meth)acrylamide, N-isopropyl(meth)acrylamide, N-(n-butyl)acrylamide, N-(sec-butyl)acrylamide, N-(tert-butyl)acrylamide and mixtures thereof.

Component b) further preferably comprises methacrylamide and/or N-(tert-butyl)acrylamide or consists of one of these components or of a mixture of methacrylamide and N-(tert-butyl)acrylamide.

Based on the total weight of the monomers used for the polymerization, the copolymers according to the invention comprise at least 2% by weight, preferably at least 4% by weight, particularly preferably at least 7% by weight and at most 25% by weight, preferably at most 20% by weight, particularly preferably at most 16% by weight and especially at most 12% by weight, of component b) in copolymerized form.

Component c)

Based on the total weight of the monomers used for the polymerization, the copolymers according to the invention comprise at least 15% by weight, preferably at least 18% by weight, particularly preferably at least 20% by weight and at most 35% by weight, preferably at most 30% by weight, particularly preferably at most 27% by weight and especially at most 25% by weight, of at least one monoethylenically unsaturated carboxylic acid as component c) in copolymerized form.

For the preparation of the copolymers, the monoethylenically unsaturated carboxylic acid c) can be used in partially or completely deprotonated form. The counterions thereof then preferably derive from bases as described below for adjusting the pH during the polymerization or of the resulting polymers.

The monoethylenically unsaturated carboxylic acid c) is chosen from the group consisting of acrylic acid, methacrylic acid, ethacrylic acid, $\alpha$-chloroacrylic acid, crotonic acid, maleic acid, maleic anhydride, itaconic acid, citraconic acid, mesaconic acid, glutaconic acid, aconitic acid and fumaric acid. The components c) further include the half-esters of monoethylenically unsaturated dicarboxylic acids having 4 to 10, preferably 4 to 6, carbon atoms, e.g. of maleic acid, such as monomethyl maleate. c) also includes the salts of the abovementioned acids, in particular the sodium, potassium and ammonium salts. The components c) can be used as they are or as a mixture with one another. The weight fractions given all refer to the acid form.

Component c) is preferably chosen from the group consisting of acrylic acid, methacrylic acid, ethacrylic acid, $\alpha$-chloroacrylic acid, crotonic acid, maleic acid, maleic anhydride, fumaric acid, itaconic acid, citraconic acid, mesaconic acid, glutaconic acid, aconitic acid and mixtures thereof, particularly preferably acrylic acid, methacrylic acid and their binary mixtures and especially methacrylic acid.

The invention preferably provides a copolymer according to the invention where component c) consists of methacrylic acid or a mixture of methacrylic acid and at least one further monoethylenically unsaturated carboxylic acid.

In particular, c) is methacrylic acid or a mixture of methacrylic acid and acrylic acid.

In a preferred embodiment of the invention, the weight ratio of methacrylic acid to the at least one further monoethylenically unsaturated carboxylic acid is at least greater than 1, preferably greater than 2, particularly preferably greater than 3.

A preferred embodiment of the invention is copolymers obtainable by free-radical polymerization of a monomer mixture M comprising
a) 50-80% by weight of ethyl methacrylate,
b) 2-15% by weight of methacrylamide and
c) mixture of 15-25% by weight of methacrylic acid and 1-10% by weight of acrylic acid.

A further preferred embodiment of the invention is copolymers obtainable by free-radical polymerization of a monomer mixture M comprising
a) 50-80% by weight of ethyl methacrylate,
b) 3-25% by weight of N-tert-butylacrylamide and
c) 15-30% by weight of methacrylic acid.

A further preferred embodiment of the invention is copolymers obtainable by free-radical polymerization of a monomer mixture M comprising
a) 50-80% by weight of ethyl methacrylate,
b) 3-25% by weight of N-tert-butylacrylamide and
c) mixture of 15-25% by weight of methacrylic acid and 1-10% by weight of acrylic acid.

Component d)

The copolymers according to the invention can additionally comprise 0 to 10% by weight of at least one compound with a free-radically polymerizable $\alpha,\beta$-ethylenically unsaturated double bond in copolymerized form.

Preferably, this component d) comprises a cationogenic and/or cationic group per molecule.

The cationogenic and/or cationic groups of component d) are preferably nitrogen-containing groups, such as primary, secondary and tertiary amino groups, and quaternary ammonium groups. The nitrogen-containing groups are preferably tertiary amino groups. Preference is given to using the compounds d) in uncharged form for the polymerization. However, a use in charged form is also suitable. Charged cationic groups can be produced, for example, from the amine nitrogens by protonation, e.g. with monobasic or polybasic carboxylic acids, such as lactic acid or tartaric acid, or mineral acids, such as phosphoric acid, sulfuric acid and hydrochloric acid.

Preferably, component d) is chosen from esters of α,β-ethylenically unsaturated mono- and dicarboxylic acids with aminoalcohols, which may be mono- or dialkylated on the amine nitrogen, amides of α,β-ethylenically unsaturated mono- and dicarboxylic acids with diamines which have at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds and mixtures thereof.

Suitable compounds d) are the esters of α,β-ethylenically unsaturated mono- and dicarboxylic acids with aminoalcohols. Preferred aminoalcohols are $C_2$-$C_{12}$-aminoalcohols which are $C_1$-$C_8$-mono- or dialkylated on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid or mixtures thereof. Particularly preferred compounds d) are N-methylaminoethyl (meth)acrylate, N-ethylaminoethyl(meth)acrylate, N-(n-propyl)aminoethyl (meth)acrylate, N-(n-butyl)aminoethyl (meth)acrylate, N-(tert-butyl)aminoethyl (meth)acrylate, N,N-dimethylaminomethyl(meth)acrylate, N,N-dimethylaminoethyl (meth)acrylate, N,N-diethylaminoethyl(meth) acrylate, N,N-dimethylaminopropyl (meth)acrylate, N,N-diethylaminopropyl(meth)acrylate and N,N-dimethylaminocyclohexyl (meth)acrylate. In particular, N-(tert-butyl)aminoethyl acrylate and N-(tert-butyl)aminoethyl methacrylate are used as compound d).

Suitable monomers d) are also the amides of the above-mentioned α,β-ethylenically unsaturated mono- and dicarboxylic acids with diamines which have at least one primary or secondary amino group. Preference is given to diamines which have one tertiary and one primary or secondary amino group. As monomers e), preference is given to using N-[2-(dimethylamino)ethyl]acrylamide, N-[2-(dimethylamino) ethyl]meth-acrylamide, N-[3-(dimethylamino)propyl]acrylamide, N-[3-(dimethylamino)propyl]meth-acrylamide, N-[4-(dimethylamino)butyl]acrylamide, N-[4-(dimethylamino)butyl]meth-acrylamide, N-[2-(diethylamino)ethyl] acrylamide, N-[4-(dimethylamino)cyclohexyl]-acrylamide and N-[4-(dimethylamino)cyclohexyl]methacrylamide. Particular preference is given to using N-[3-(dimethylamino) propyl]acrylamide and/or N-[3-(dimethylamino)propyl] methacrylamide.

Suitable monomers d) are also N,N-diallylamines and N,N-diallyl-N-alkylamines and acid addition salts thereof. Alkyl here is preferably $C_1$-$C_{24}$-alkyl. Preference is given, for example, to N,N-diallyl-N-methylamine.

Suitable monomers d) are also vinyl- and allyl-substituted nitrogen heterocycles, such as N-vinylimidazole, N-vinylimidazole derivatives, e.g. N-vinyl-2-methylimidazole, vinyl- and allyl-substituted heteroaromatic compounds, such as 2- and 4-vinylpyridine, 2- and 4-allylpyridine, and the salts thereof.

Suitable monomers d) are also N-vinylimidazoles of the general formula (II) in which $R^1$ to $R^3$ is hydrogen, $C_1$-$C_4$-alkyl or phenyl

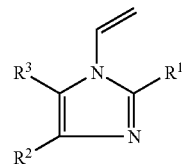

(II)

Examples of compounds of the general formula (II) are given in Table 1 below:

TABLE 1

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Particular preference is given to the compounds of component d) chosen from N-(tert-butylamino)ethyl(meth)acrylate, N,N-dimethylaminoethyl(meth)acrylate, N-[3-(dimethylamino)propyl](meth)acrylamide, vinylimidazole and mixtures thereof.

The copolymers according to the invention comprise at most 10% by weight, particularly preferably at most 7% by weight, in particular at most 5% by weight, based on the total weight of the monomers used for the polymerization, of at least one monomer d) in copolymerized form. If a monomer d) is used, then it is preferably in an amount of at least 0.5% by weight, particularly preferably at least 2% by weight and especially at least 3% by weight.

In a preferred embodiment, the copolymers according to the invention comprise a) ethyl methacrylate, b) methacrylamide and/or N-(tert-butyl)acrylamide, c) methacrylic acid or a mixture of methacrylic acid and acrylic acid and if appropriate a further monomer d) chosen from the group consisting of N-[3-(dimethylamino)propyl](meth)-acrylamide, N-(tert-butyl)aminoethyl methacrylate, vinylimidazole and mixtures thereof, in copolymerized form.

A preferred embodiment of the invention is copolymers comprising
a) 60 to 75% by weight of ethyl methacrylate,
b) 7 to 15% by weight of at least one compound b),
c) 18 to 27% by weight of at least one compound c) and
d) 0 to 15% by weight of at least one compound d).

A further preferred embodiment of the invention is copolymers comprising
a) 60 to 70% by weight of ethyl methacrylate,
b) 8 to 12% by weight of at least one compound b),
c) 20 to 25% by weight of at least one compound c) and
d) 0 to 10% by weight of at least one compound d).

A further preferred embodiment of the invention is copolymers comprising
a) 50 to 80% by weight of ethyl methacrylate,
b) 2 to 15% by weight of methacrylamide,
c) 15 to 25% by weight of methacrylic acid and 1 to 10% by weight of acrylic acid.

A further preferred embodiment of the invention is copolymers comprising
a) 50 to 80% by weight of ethyl methacrylate,
b) 3 to 25% by weight of N-(tert-butyl)acrylamide,
c) 15 to 30% by weight of methacrylic acid.

A further preferred embodiment of the invention is copolymers comprising
a) 50 to 80% by weight of ethyl methacrylate,
b) 3 to 25% by weight of N-(tert-butyl)acrylamide,
c) 15 to 25% by weight of methacrylic acid and 1 to 10% by weight of acrylic acid.

A further preferred embodiment of the invention is copolymers comprising
a) 50 to 80% by weight of ethyl methacrylate,
b) 3 to 25% by weight of N-(tert-butyl)acrylamide,
c) 15 to 30% by weight of methacrylic acid and
d) 1 to 7% by weight of monomer chosen from the group consisting of N-[3-(dimethylamino)propyl](meth)acrylamide, N-(tert-butyl)aminoethyl methacrylate, vinylimidazole and mixtures thereof.

The copolymers according to the invention can additionally comprise, in copolymerized form, a monomer e) different from components a) to d) and copolymerizable therewith.

Component e) is preferably chosen from esters of α,β-ethylenically unsaturated mono- and dicarboxylic acids with $C_1$-$C_{30}$-alkanols and $C_1$-$C_{30}$-alkanediols, amides of α,β-ethylenically unsaturated mono- and dicarboxylic acids with $C_2$-$C_{30}$-aminoalcohols which have a primary or secondary amino group, N-vinyllactams, N-vinylamides of saturated monocarboxylic acids, primary amides of α,β-ethylenically unsaturated monocarboxylic acids and N-alkyl and N,N-dialkyl derivatives thereof, esters of vinyl alcohol and allyl alcohol with $C_1$-$C_{30}$-monocarboxylic acids, vinyl ethers, vinyl aromatics, vinyl halides, vinylidene halides, $C_1$-$C_8$-monoolefins, nonaromatic hydrocarbons with at least two conjugated double bonds and mixtures thereof.

N-vinyllactams suitable as monomers e) are unsubstituted N-vinyllactams and N-vinyllactam derivatives which can have, for example, one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc.

In a preferred embodiment, the copolymers according to the invention comprise no N-vinyllactams in copolymerized form.

N-vinylamide compounds suitable as monomers e) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide. In a preferred embodiment, the copolymers according to the invention comprise no N-vinylamide compounds in copolymerized form.

Suitable additional monomers e) are also 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable additional monomers e) are also 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Suitable monomers e) are also polyether acrylates, which, for the purposes of this invention, are generally understood as meaning esters of α,β-ethylenically unsaturated mono- and dicarboxylic acids with polyetherols. Suitable polyetherols are linear or branched substances having terminal hydroxyl groups and comprising ether bonds. In general, they have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for preparing alkylene oxide copolymers are, for example, ethylene oxide, propylene oxide, epichlorohydrin, 1,2- and 2,3-butylene oxide. The alkylene oxide copolymers can comprise the copolymerized alkylene oxide units in random distribution or in the form of blocks. Preference is given to ethylene oxide/propylene oxide copolymers.

As component e), preference is given to polyether acrylates of the general formula III

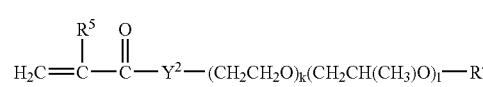

(III)

in which
the order of the alkylene oxide units is arbitrary,
k and l, independently of one another, are an integer from 0 to 1000, the sum of k and l being at least 5,
$R^4$ is hydrogen, $C_1$-$C_{30}$-alkyl or $C_5$-$C_8$-cycloalkyl,
$R^5$ is hydrogen or $C_1$-$C_8$-alkyl,
$Y^2$ is O or $NR^6$, where $R^6$ is hydrogen, $C_1$-$C_{30}$-alkyl or $C_5$-$C_8$-cycloalkyl.

Preferably, k is an integer from 1 to 500, in particular 3 to 250. Preferably, l is an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

Preferably, $R^4$ in the formula II is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably, $Y^2$ in the formula III is O or NH.

Suitable polyetheracrylates e) are, for example, the polycondensation products of the abovementioned α,β-ethylenically unsaturated mono- and/or dicarboxylic acids and the acid chlorides, amides and anhydrides thereof with polyetherols. Suitable polyetherols can be prepared easily by reacting ethylene oxide, 1,2-propylene oxide and/or epichlorohydrin with a starter molecule, such as water or a short-chain alcohol $R^4$—OH. The alkylene oxides can be used individually, alternately one after the other or as a mixture.

The polyether acrylates e) can be used on their own or in mixtures for preparing the polymers used according to the invention.

Suitable additional monomers e) are the esters of α,β-ethylenically unsaturated mono- and dicarboxylic acids different from ethyl methacrylate, such as, for example, methyl (meth)acrylate, ethyl acrylate, methyl ethacrylate, n-propyl (meth)acrylate, isopropyl (meth)acrylate, n-propyl ethacrylate, ethyl ethacrylate, isopropyl ethacrylate, n-butyl (meth)acrylate, n-butyl ethacrylate, tert-butyl(meth)acrylate, tert-butyl ethacrylate, isobutyl(meth)acrylate, isobutyl ethacrylate, sec-butyl(meth)acrylate, butyl ethacrylate, 2-pentyl(meth)acrylate, 3-pentyl(meth)acrylate, isopentyl acrylate, neopentyl acrylate, n-octyl(meth)acrylate, 1,1,3,3-tetramethylbutyl(meth)acrylate, ethylhexyl (meth)acrylate, n-nonyl(meth)acrylate, n-decyl(meth)acrylate, n-undecyl (meth)acrylate, tridecyl(meth)acrylate, myristyl(meth)acrylate, pentadecyl (meth)acrylate, palmityl(meth)acrylate, heptadecyl(meth)acrylate, nonadecyl (meth)acrylate, arrachinyl (meth)acrylate, behenyl(meth)acrylate, lignocerenyl (meth) acrylate, cerotinyl(meth)acrylate, melissinyl(meth)acrylate, palmitoleinyl (meth)acrylate, oleyl(meth)acrylate, linolyl (meth)acrylate, linolenyl(meth)acrylate, stearyl(meth)acrylate, lauryl(meth)acrylate, phenoxyethyl acrylate, t-butylcyclohexyl acrylate, cyclohexyl(meth)acrylate, ureido (meth) acrylate, tetrahydrofurfuryl (meth)acrylate and mixtures thereof.

Preferred monomers e) are the esters of α,β-ethylenically unsaturated mono- and dicarboxylic acids with $C_1$-$C_4$-alkanols.

Suitable additional monomers e) are also N-(n-butyl)methacrylamide, N-(sec-butyl)methacrylamide, N-(tert-butyl)methacrylamide, N-(n-pentyl)(meth)acrylamide, N-(n-hexyl)(meth)acrylamide, N-(n-heptyl)(meth)acrylamide, N-(n-octyl)(meth)acrylamide, N-(tert-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth) acrylamide, N-heptadecyl(meth)acrylamide, N-nonadecyl (meth)acrylamide, N-arrachinyl(meth)acrylamide, N-behenyl(meth)acrylamide, N-lignocerenyl(meth)acrylamide, N-cerotinyl(meth)acrylamide, N-melissinyl(meth)acrylamide, N-palmitoleinyl(meth)acrylamide, N-oleyl (meth)acrylamide, N-linolyl(meth)acrylamide, N-linolenyl (meth)acrylamide, N-stearyl(meth)acrylamide, N-lauryl (meth)acrylamide.

Suitable additional monomers e) are also vinyl acetate, vinyl propionate, vinyl butyrate and mixtures thereof.

Suitable additional monomers e) are also ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The abovementioned additional monomers e) can be used individually or in the form of any desired mixtures.

The copolymers according to the invention comprise at most 10% by weight, particularly preferably at most 7% by weight, in particular at most 5% by weight, based on the total weight of the monomers used for the polymerization, of at least one monomer e) in copolymerized form. If a monomer e) is used, then it is preferably in an amount of at least 0.5% by weight, particularly preferably at least 2% by weight and in particular at least 3% by weight.

Crosslinker f)

If desired, the copolymers according to the invention can comprise at least one crosslinker, i.e. a compound with two or more than two ethylenically unsaturated, nonconjugated double bonds in copolymerized form.

Preferably, crosslinkers are used in an amount of from 0.01 to 3% by weight, particularly preferably 0.1 to 2% by weight, based on the total weight of the monomers used for the polymerization.

Suitable crosslinkers f) are, for example, acrylic esters, methacrylic esters, allyl ethers or vinyl ethers of at least dihydric alcohols. The OH groups of the parent alcohols may here be completely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans with molecular weights of in each case from 200 to 10 000. Apart from the homopolymers of ethylene oxide and/or propylene oxide it is also possible to use block copolymers of ethylene oxide or propylene oxide or copolymers which comprise ethylene oxide and propylene oxide groups in incorporated form. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. The polyhydric alcohols can of course also be used following reaction with ethylene oxide or propylene oxide as the corresponding ethoxylates or propoxylates, respectively. The polyhydric alcohols can also firstly be converted to the corresponding glycidyl ethers by reaction with epichlorohydrin.

Further suitable crosslinkers f) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric unsaturated alcohols with polybasic carboxylic acids, for example malonic acid, tartaric acid, trimellitic acid, phthalic acid, terephthalic acid, citric acid or succinic acid.

Further suitable crosslinkers f) are esters of unsaturated carboxylic acids with the above-described polyhydric-alcohols, for example of oleic acid, crotonic acid, cinnamic acid or 10-undecenoic acid.

Further suitable crosslinkers f) are urethane diacrylates and urethane polyacrylates, as are commercially available, for example, under the name Laromer®.

Suitable crosslinkers f) are also straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Further suitable crosslinkers f) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids as have been described above.

Triallylamine and triallylmonoalkylammonium salts, e.g. triallylmethylammonium chloride or methylsulfate, are also suitable crosslinkers f).

Also suitable are N-vinyl compounds of urea derivatives, at least difunctional amides, cyanurates or urethanes, for example of urea, ethyleneurea, propyleneurea or tartramide, e.g. N,N'-divinylethyleneurea or N,N'-divinylpropyleneurea.

Further suitable crosslinkers f) are divinyidioxane, tetraallylsilane or tetravinylsilane.

It is of course also possible to use mixtures of the abovementioned compounds f). Preference is given to using water-soluble crosslinkers f).

Crosslinkers f) used particularly preferably are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Very particularly preferred crosslinkers f) are pentaerythritol triallyl ether, methylenebis-acrylamide, N,N'-divinylethyleneurea, triallylamine and triallylmonoalkylammonium salts and acrylic esters of glycol, butanediol, trimethylolpropane or glycerol or acrylic esters of glycol, butanediol, trimethylolpropane or glycerol reacted with ethylene oxide and/or epichlorohydrin.

A preferred embodiment of the invention is copolymers obtainable by free-radical polymerization of a monomer mixture M comprising a) 40 to 80% by weight of ethyl methacrylate,
b) 5 to 20% by weight of methacrylamide and/or N-(tert-butyl)acrylamide,
c) 15 to 30% by weight of methacrylic acid or a mixture of methacrylic acid and acrylic acid,
d) 0 to 10% by weight of N-[3-(dimethylamino)propyl](meth)acrylamide.

A particularly preferred embodiment of the invention is copolymers obtainable by free-radical polymerization of a monomer mixture M comprising a) 60 to 70% by weight of ethyl methacrylate,
b) 7 to 15% by weight of methacrylamide
c) c1) 12 to 18% by weight of methacrylic acid c2) 4 to 9% by weight of acrylic acid,
d) 1 to 3% by weight of N-[3-(dimethylamino)propyl](meth)acrylamide.

Preparation of the Copolymers

The copolymers according to the invention can be prepared, for example, by solution, precipitation, suspension or emulsion polymerization. Such processes are known in principle to the person skilled in the art. Preference is given to preparation by solution polymerization.

Preferred solvents for the polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, polyethylene glycols with number-average molecular weights up to about 3000, glycerol and dioxane.

The polymerization is particularly preferably in water or a water/alcohol mixture, for example in a water/ethanol mixture.

The polymerization can in principle be carried out at the pH resulting from the monomers used. If at least one N-vinyllactam is used for the polymerization (=component e)), then the pH of the polymerization medium is preferably adjusted to a value of from 5 to 8, preferably 6 to 7. It is advantagoues to then keep the pH in this range throughout the polymerization. Of suitability for adjusting the pH before, during or after the polymerization are, in principle, all inorganic or organic bases (and if appropriate acids), in particular those which, apart from a possible salt formation, do not undergo reaction with the monomers. Suitable bases are, for example, alkali metal and alkaline earth metal hydroxides, ammonia, and primary, secondary and tertiary amines, such as triethylamine, and aminoalcohols, such as triethanolamine, methyldiethanolamine, dimethylethanolamine or 2-amino-2-methylpropanol. For adjusting the pH, preference is given to using at least one tertiary amine, which is chosen in particular from N,N-dimethylethanolamine, N-methyldiethanolamine, triethanolamine and mixtures thereof. If, for the polymerization, at least one N-vinyllactam is used (=component e)), then the pH of the polymerization medium is preferably adjusted using N,N-dimethylethanolamine.

The polymerization temperatures are preferably in a range from about 30 to 120° C., particularly preferably 40 to 100° C. The polymerization is usually carried out under atmospheric pressure, although it can also proceed under reduced or elevated pressure. A suitable pressure range is between 1 and 5 bar.

For the copolymerization, the monomers can be polymerized using initiators which form free radicals.

Initiators for the free-radical polymerization which may be used here are the peroxo and/or azo compounds customary for this purpose, for example alkali metal or ammonium peroxidisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxidicarbamate, bis-(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis (2-amidinopropane) hydrochloride (V50 from Wako Pure Chemicals Industries, Ltd.), or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate, $H_2O_2/Cu^I$.

To adjust the molecular weight, the polymerization can be carried out in the presence of at least one regulator. Regulators which may be used are the customary compounds known to the person skilled in the art, such as, for example, sulfur compounds, e.g. mercaptoethanol, 2-ethylhexyl thioglycolate, thioglycolic acid or dodecylmercaptan, and tribromochloromethane or other compounds which have a regulating effect on the molecular weight of the resulting polymers. A preferred regulator is cysteine.

To achieve the purest possible polymers with a low residual monomer content, the polymerization (main polymerization) can be followed by an after-polymerization step. The after-polymerization can take place in the presence of the same initiator system as the main polymerization or a different initiator system. Preferably, the after-polymerization is carried out at the same temperature as the main polymerization, preferably at a higher temperature. If desired, the reaction mixture can be subjected to stripping with steam or to steam distillation following the polymerization or between the first and the second polymerization steps.

The polymerization can in principle be carried out at the pH resulting from the monomers used. If, for the polymerization, at least one N-vinyllactam is used (=component e)), then the pH of the polymerization medium is preferably adjusted to a value of from 5 to 8, preferably 6 to 7. It is advantageous to then keep the pH in this range throughout the polymerization. Of suitability for adjusting the pH before, during or after the polymerization are in principle all inorganic or organic bases (and if appropriate acids), in particular those which, apart from a possible salt formation, do not undergo reaction with the monomers. Suitable neutralizing agents are described below.

If, in the preparation of the polymers, an organic solvent is used, then this can be removed by customary processes known to the person skilled in the art, e.g. by distillation at reduced pressure.

Neutralization

Moreover, the polymers present can be partially or completely neutralized. For using the polymers in hair cosmetic preparations in particular, partial or complete neutralization is advantageous.

In preferred embodiments, the polymers are neutralized for example to at least 10%, preferably to at least 30%, further preferably to at least 40%, particularly preferably to at least 50%, very particularly preferably to at least 70% and especially to at least 95%.

In a particularly preferred embodiment, the polymers are neutralized to at least 99%. Most preferably, the neutralization is to at least 100%.

It is further advantageous if the neutralizing agent is added in more than an equivalent amount, equivalent amount being understood as meaning the amount which is required to neutralize all of the neutralizable groups of the polymers.

The neutralization can also take place with
a mono-, di- or trialkanolamine with 2 to 5 carbon atoms in the alkanol radical which, if appropriate, is in etherified form, for example mono-, di- and triethanolamine, mono-, di- and tri-n-propanolamine, mono-, di- and tri-iso-propanolamine, 2-amino-2-methylpropanol and di(2-methoxyethyl)amine,
an alkanediolamine with 2 to 5 carbon atoms, for example 2-amino-2-methylpropane-1,3-diol and 2-amino-2-ethylpropane-1,3-diol, or
a primary, secondary or tertiary alkylamine with a total of 5 to 10 carbon atoms, for example N,N-diethylpropylamine or 3-diethylamino-1-propylamine.

Suitable alkali metal hydroxides for the neutralization are primarily sodium hydroxide or potassium hydroxide and ammonium hydroxide.

Good neutralization results are often obtained with 2-amino-2-methylpropanol, triiso-propanolamine, 2-amino-2-ethylpropane-1,3-diol, N,N-dimethylaminoethanol or 3-di-ethylamino-1-propylamine.

Also suitable for neutralizing the polymers in the preparations and compositions according to the invention are, in particular, silicone polymers comprising amino groups. Suitable silicone polymers comprising amino groups are, for example, the silicone-aminopolyalkylene oxide block copolymers of WO 97/32917, the products Silsoft® A-843 (Dimethicone Bisamino Hydroxypropyl Copolyol) and Silsoft® A-858 (Trimethylsilyl A modi methicone Copolymer) (both Witco). Further suitable are also the neutralization polymers of EP-A 1035144 and in particular the silicone-containing neutralization polymers according to claim 12 of EP-A 1035144.

The liquid polymer compositions obtained can be converted to powder form by various drying methods, such as, for example, spray drying, fluidized spray drying, drum drying or freeze drying. Preference is given to using spray drying. The dry polymer powders obtained in this way can advantageously be converted again to an aqueous solution or dispersion by dissolution or redispersion, respectively, in water. Pulverulent copolymers have the advantage of better storability, simpler transportation option and generally exhibit a lower propensity for microbial attack.

Cosmetic and Pharmaceutical Compositions

The copolymers described above are exceptionally suitable for preparing cosmetic and pharmaceutical compositions. They serve here, for example, as polymeric film formers in preparations for bodycare, which includes application in cosmetic preparations for keratinous surfaces such as skin, hair, nails, and also mouthcare preparations. They can be used and formulated universally into a very wide range of cosmetic preparations and are compatible with the customary components. In particular, the copolymers according to the invention are suitable for preparing hair cosmetic compositions. Compared with customary polymers known from the prior art, they are advantageously suitable for creating elastic hairstyles coupled with strong hold (even at high atmospheric humidity). The copolymers according to the invention are also characterized by good propellant gas compatibility, good solubility in water or aqueous/alcoholic solvent mixtures, suitability for use in low-VOC formulations and good ability to be washed out. In addition, they usually also have good conditioning properties, i.e. they improve hair treated therewith in its sensory properties, such as feel, volume, handability etc. Hairspray formulations based on the copolymers according to the invention are characterized by good rheological properties and good sprayability.

Cosmetically or Pharmaceutically Acceptable Carrier B)

The compositions according to the invention have a cosmetically or pharmaceutically acceptable carrier B) which is chosen from
i) water,
ii) water-miscible organic solvents, preferably $C_2$-$C_4$-alkanols, in particular ethanol,
iii) oils, fats, waxes,
iv) esters of $C_6$-$C_{30}$-monocarboxylic acids with mono-, di- or trihydric alcohols which are different from iii),
v) saturated acyclic and cyclic hydrocarbons,
vi) fatty acids,
vii) fatty alcohols,
viii) propellant gases and mixtures thereof.

The compositions according to the invention have, for example, an oil or fat component B) which is chosen from: hydrocarbons of low polarity, such as mineral oils; linear saturated hydrocarbons, preferably with more than 8 carbon atoms, such as tetradecane, hexadecane, octadecane etc.; cyclic hydrocarbons, such as decahydronaphthalene; branched hydrocarbons; animal and vegetable oils; waxes; wax esters; vaseline; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methyl-phenylsiloxanes), cyclic siloxanes and mixtures thereof. The number-average molecular weight of the polydimethylsiloxanes and poly(methylphenylsiloxanes) is preferably in a range from about 1000 to 150 000 g/mol. Preferred cyclic siloxanes have 4- to 8-membered rings. Suitable cyclic siloxanes are commercially available, for example, under the name cyclomethicone.

Preferred oil or fat components B) are chosen from paraffin and paraffin oils; vaseline; natural fats and oils, such as castor oil, soya oil, peanut oil, olive oil, sunflower oil, sesame oil, avocado oil, cocobutter, almond oil, peach kernel oil, ricinus oil, cod-liver oil, pork lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids, different therefrom; waxes, such as beeswax, carnauba wax, candililla wax, spermaceti, and mixtures of the abovementioned oil and fat components.

Suitable cosmetically and pharmaceutically compatible oil and fat components B) are described in Karl-Heinz Schrader, Grundlagen und Rezepturen der Kosmetika [Fundamentals and formulations of cosmetics], $2^{nd}$ edition, Verlag Huthig, Heidelberg, pp. 319-355, to which reference is hereby made.

Suitable hydrophilic carriers B) are chosen from water, 1-, 2- or polyhydric alcohols having preferably 1 to 8 carbon atoms, such as ethanol, n-propanol, isopropanol, propylene glycol, glycerol, sorbitol, etc.

The cosmetic compositions according to the invention may be skin cosmetic, hair cosmetic, dermatological, hygiene or pharmaceutical compositions. On account of their film-forming properties, the copolymers described above are suitable in particular as additives for hair and skin cosmetics.

Preferably, the compositions according to the invention are in the form of a spray, gel, foam, an ointment, cream, emulsion, suspension, lotion, milk or paste. If desired, liposomes or microspheres can also be used.

In a preferred embodiment of the invention, the compositions have a content of volatile organic components of at most 80% by weight, preferably at most 55% by weight and in particular at most 30% by weight. A preferred subject-matter is thus compositions which correspond to the low-VOC standard, i.e. VOC-80 and VOC-55 standard.

The cosmetically or pharmaceutically active compositions according to the invention can additionally comprise cosmetically and/or dermatologically active ingredients and auxiliaries.

Preferably, the cosmetic compositions according to the invention comprise at least one copolymer as defined above (=component A), at least one carrier B) as defined above and at least one constituent different therefrom which is chosen from cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, bodying agents, humectants, regreasing agents, collagen, protein hydrolyzates, lipids, antioxidants, antifoams, antistats, emollients and softeners.

Thickeners

Customary thickeners in such formulations are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Preference is given to using nonionic thickeners.

Cosmetically and/or Dermatologically Active Ingredients

Suitable cosmetically and/or dermatologically active ingredients are, for example, coloring active ingredients, skin and hair pigmentation agents, tinting agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinising substances, antioxidative active ingredients and active ingredients acting as free-radical scavengers, skin moisturizing or humectant substances, regreasing active ingredients, antierythematous or antiallergic active ingredients and mixtures thereof.

Artificially skin-tanning active ingredients which are suitable for tanning the skin without natural or artificial exposure to UV rays are, for example, dihydroxyacetone, alloxan and walnut shell extract. Suitable keratin-hardening substances are generally active ingredients as are also used in antiperspirants, such as, for example, potassium aluminum sulfate, aluminum hydroxychloride, aluminum lactate, etc. Antimicrobial active ingredients are used for destroying microorganisms and/or for inhibiting their growth and thus serve both as preservative and also as deodorizing substance which reduces the formation or the intensity of body odor. These include, for example, customary preservatives known to the person skilled in the art, such as p-hydroxybenzoic esters, imidazolidinyl urea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc.

Suitable photofilter active ingredients are substances which absorb UV rays in the UV-B and/or UV-A region. Suitable UV filters are, for example, 2,4,6-triaryl-1,3,5-triazines in which the aryl groups can in each case carry at least one substituent which is preferably chosen from hydroxy, alkoxy, specifically methoxy, alkoxycarbonyl, specifically methoxycarbonyl and ethoxycarbonyl and mixtures thereof. Also suitable are p-aminobenzoic esters, cinnamic esters, benzophenones, camphor derivatives, and pigments which deter UV rays, such as titanium dioxide, talc and zinc oxide. Examples of UV photoprotective filters are:

| No. | Substance | CAS No. |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |

| No. | Substance | CAS No. |
|---|---|---|
| 4 | 2-Hydroxy-4-methoxybenzophenone(oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfo)benzylidene-bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianiline-(o-carbo-2'-ethylhexyl-1'-oxy)-1,3,5-triazine | 88122-99-0 |
| 18 | 3-Imidazol-4-ylacrylic acid and its ethyl ester | 104-98-3 |
| 19 | Menthyl o-aminobenzoates or: 5-methyl-2-(1-methylethyl) 2-aminobenzoate | 134-09-8 |
| 20 | Glyceryl p-aminobenzoate or 1-glyceryl 4-aminobenzoate | 136-44-7 |
| 21 | 2,2'-Dihydroxy-4-methoxybenzophenone (dioxybenzone) | 131-53-3 |
| 22 | 2-Hydroxy-4-methoxy-4-methylbenzophenone (mexenone) | 1641-17-4 |
| 23 | Triethanolamine salicylate | 2174-16-5 |
| 24 | Dimethoxyphenylglyoxalic acid or: sodium 3,4-dimethoxyphenylglyoxalate | 4732-70-1 |
| 25 | 3-(4'Sulfo)benzylidenebornan-2-one and its salts | 56039-58-8 |
| 26 | 2,2',4,4'-Tetrahydroxybenzophenone | 131-55-5 |
| 27 | 2,2'-Methylenebis[6(2H-benzotriazol-2-y)-4-(1,1,3,3,-tetramethylbutyl)phenol] | 103597-45-1 |
| 28 | 2,2'-(1,4-Phenylene)-bis-1H-benzimidazole-4,6-disulfonic acid, Na salt | 180898-37-7 |
| 29 | 2,4-bis-[4-(2-Ethyl hexyloxy)-2-hydroxy]phenyl-6-(4-methoxyphenyl)-(1,3,5)-triazine | 187393-00-6 |
| 30 | 3-(4-Methylbenzylidene)camphor | 36861-47-9 |
| 31 | Polyethoxyethyl 4-bis(polyethoxy)paraaminobenzoate | 113010-52-9 |
| 32 | 2,4-Dihydroxybenzophenone | 131-56-6 |
| 33 | 2,2'-Dihydroxy-4,4'-dimethoxybenzophenone 5,5'-disodium sulfonate | 3121-60-6 |

Further combinable photoprotective agents are, inter alia, the following compounds:

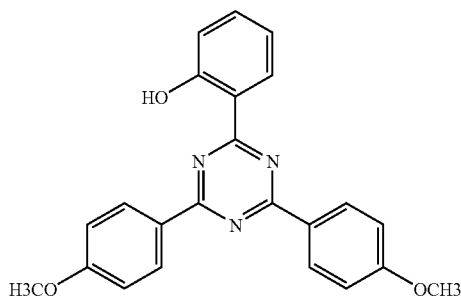

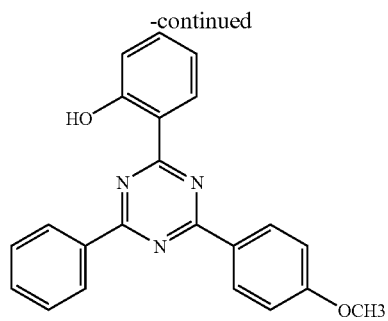

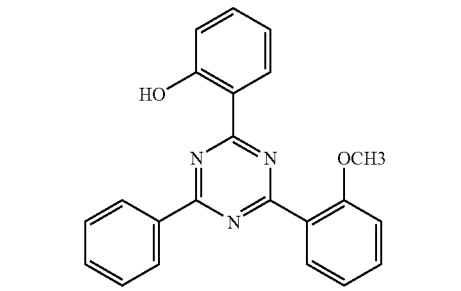

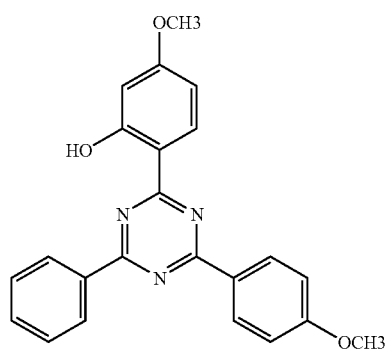

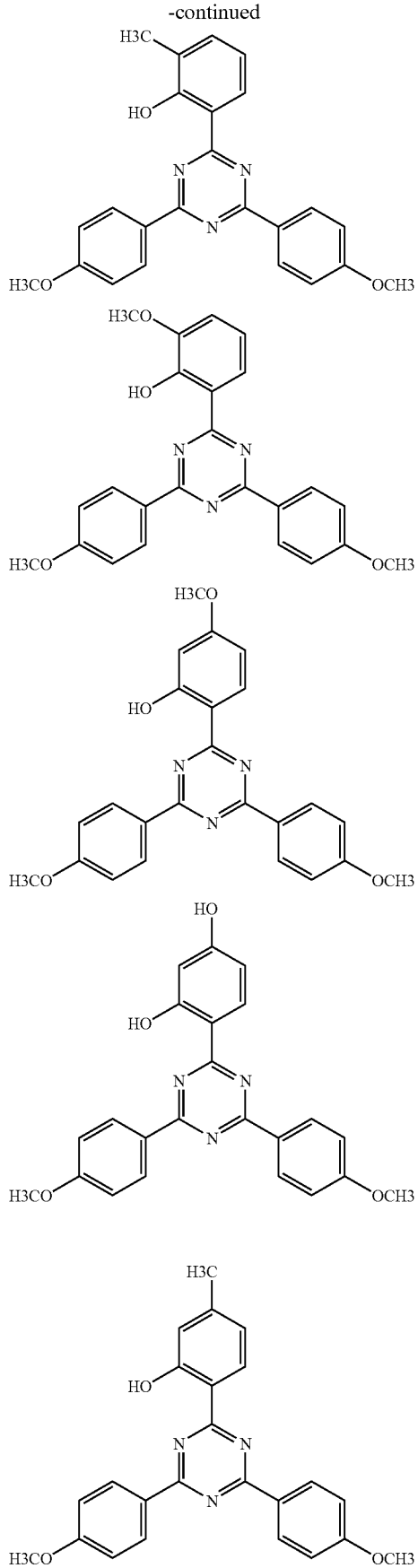
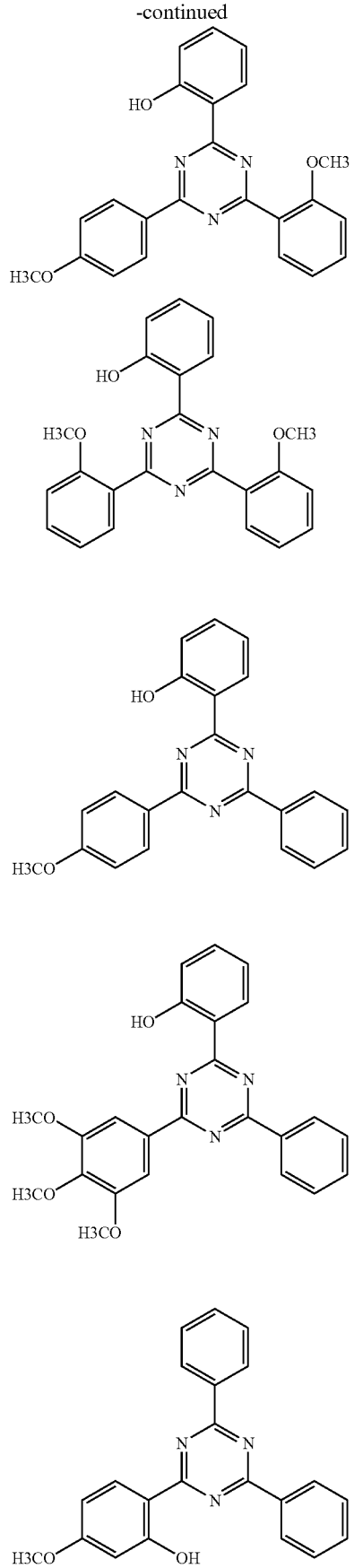

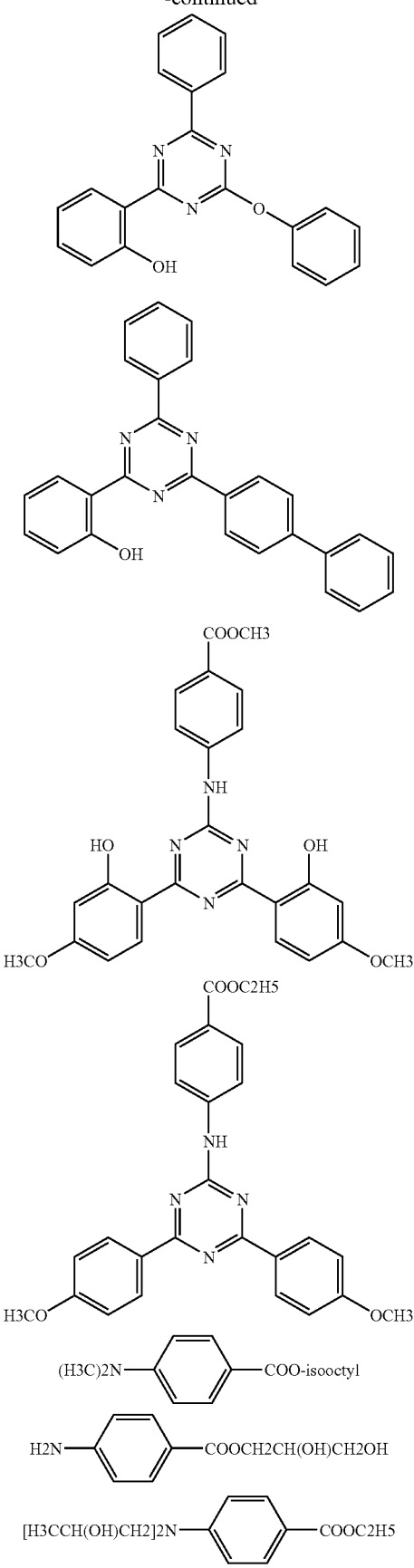

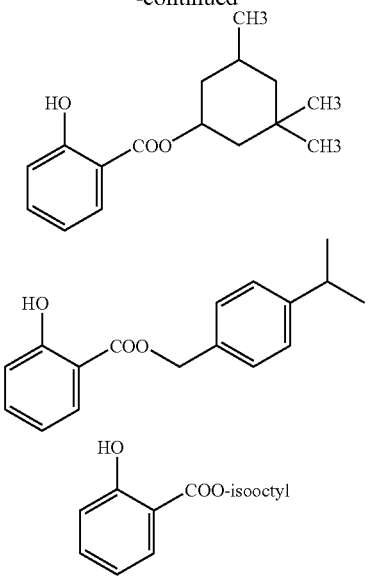

Also suitable are pigments which deter UV rays, such as titanium dioxide, talc and zinc oxide.

Photoprotective agents suitable for use in the preparations according to the invention are also the compounds specified in EP-A 1 084 696 in paragraphs [0036] to [0053], the entire contents of which are hereby incorporated by reference.

The list of specified UV photoprotective filters which can be used in the preparations according to the invention is not of course intended to be limiting.

Antimicrobial Agents

In addition, antimicrobial agents can also be used in the preparations according to the invention. In general, these include all suitable preservatives with a specific action against Gram-positive bacteria, e.g. triclosan (2,4,4'-trichloro-2'-hydroxydiphenyl ether), chlorhexidine (1,1'-hexamethylenebis[5-(4-chlorophenyl)biguanide) and TTC (3,4,4'-trichlorocarbanilide).

Quarternary ammonium compounds are in principle likewise suitable, but are preferably used for disinfecting soaps and washing lotions.

Numerous fragrances also have antimicrobial properties. Special combinations with particular effectiveness toward Gram-positive bacteria are used for the composition of so-called deodorant perfumes.

A large number of essential oils or their characteristic ingredients, such as, for example, oil of cloves (eugenol), mint oil (menthol) or thyme oil (thymol), also exhibit marked antimicrobial effectiveness.

The antibacterially effective substances are generally used in concentrations of from about 0.1 to 0.3% by weight.

Suitable repellent active ingredients are compounds which are able to deter or repel certain animals, in particular insects, from people. These include, for example, 2-ethyl-1,3-hexanediol, N,N-diethyl-m-toluamide etc.

Suitable hyperemic substances, which stimulate blood flow in the skin, are, for example, essential oils, such as dwarf pine, lavender, rosemary, juniper berry, roast chestnut extract, birch leaf extract, marigold extract, ethyl acetate, camphor, menthol, peppermint oil, rosemary extract, eucalyptus oil, etc.

Suitable keratolytic and keratoplastic substances are, for example, salicylic acid, calcium thioglycolate, thioglycolic acid and its salts, sulfur, etc.

Suitable antidandruff active ingredients are, for example, sulfur, sulfur polyethylene glycol sorbitan monooleate, sulfur ricinol polyethoxylate, zinc pyrithion, aluminum pyrithion, etc. Suitable antiphlogistics, which counteract skin irritations, are, for example, allantoin, bisabolol, dragosantol, chamomile extract, panthenol, etc.

The cosmetic compositions according to the invention can comprise, as cosmetic and/or pharmaceutical active ingredient (and also if appropriate as auxiliary), at least one cosmetically or pharmaceutically acceptable polymer.

Anionic polymers preferred as additional polymers are, for example, homopolymers and copolymers of acrylic acid and methacrylic acid, and salts thereof. These also include crosslinked polymers of acrylic acid, as available under the INCI name Carbomer. Such crosslinked homopolymers of acrylic acid are, for example, commercially available under the name Carbopol® from BF GOODRICH. Preference is also given to hydrophobically modified crosslinked polyacrylate polymers, such as Carbopol® Ultrez 21 from Noveon.

Further examples of suitable additional anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyether acrylates, where the polyether chain is terminated with a $C_8$-$C_{30}$-alkyl radical. These include, for example, acrylate/beheneth-25 methacrylate copolymers, which are available under the name Aculyn® from Rohm und Haas. Particularly suitable polymers are also copolymers of t-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate, acrylic acid (Ultrahold® 8, strong), copolymers of vinyl acetate, crotonic acid and if appropriate further vinyl esters (e.g. Luviset® grades), maleic anhydride copolymers, if appropriate reacted with alcohol, anionic polysiloxanes, e.g. carboxy functional ones, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are commercially available, for example, under the names Resyn® (National Starch) and Gafset® (GAF) and vinylpyrrolidone/vinyl acrylate copolymers, obtainable, for example, under the trade name Luviflex® (BASF). Further suitable polymers are the vinylpyrrolidone/acrylate terpolymer obtainable under the name Luviflex® VBM-35 (BASF) and sodium sulfonate-containing polyamides or sodium sulfonate-containing polyesters.

In addition, the group of suitable anionic polymers includes, for example, Balance® CR (National Starch; acrylate copolymer), Balance® 0/55 (National Starch; acrylate copolymer), Balance® 47 (National Starch; octylacrylamide/acrylate/butylaminoethyl methacrylate copolymer), Aquaflex® FX 64 (ISP; isobutylene/ethylmaleimide/hydroxyethylmaleimide copolymer), Aquaflex® SF-40 (ISP/National Starch; VP/vinyl caprolactam/DMAPA acrylate copolymer), Allianz® LT-120 (ISP; Rohm & Haas; acrylate/$C_{1-2}$ succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-7,2-(Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne® 258 (Rohm & Haas; acrylate/hydroxyl ester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), Dynamx® (National Starch; polyurethane-14 AMP-acrylates copolymer), Resyn® XP (National Starch; acrylates/octylacrylamide copolymer), Fixomer® A-30 (Ondeo Nalco; polymethacrylic acid (and) acrylamidomethylpropanesulfonic acid), Fixate® G-100 (Noveon; AMP-acrylates/allyl methacrylate copolymer).

Suitable additional polymers are also the terpolymers of vinylpyrrolidone, $C_1$-$C_{10}$-alkyl-cycloalkyl- and aryl(meth)acrylates and acrylic acid described in U.S. Pat. No. 3,405,084. Suitable additional polymers are also the terpolymers of vinylpyrrolidone, tert-butyl (meth)acrylate and (meth)acrylic acid described in EP-A-0 257 444 and EP-A-0 480 280. Suitable additional polymers are also the copolymers described in DE-A-42 23 066 which comprise at least one (meth)acrylic ester, (meth)acrylic acid and N-vinylpyrrolidone and/or N-vinylcaprolactam in copolymerized form. The disclosure of these documents is hereby incorporated by reference.

Suitable polymers containing carboxylic acid groups are also polyurethanes containing carboxylic acid groups.

EP-A-636361 discloses suitable block copolymers with polysiloxane blocks and polyurethane/polyurea blocks which have carboxylic acid and/or sulfonic acid groups. Suitable silicone-containing polyurethanes are also described in WO 97/25021 and EP-A-751 162. Suitable polyurethanes are also described in DE-A-42 25 045, which is hereby incorporated in its entirety by reference.

These polyurethanes are in principle constructed from
i) at least one compound which comprises two or more active hydrogen atoms, per molecule,
ii) at least one carboxylic-acid-group-comprising diol or a salt thereof and
iii) at least one polyisocyanate.

Component i) is, for example, a diol, diamine, amino alcohol, or mixture thereof. The molecular weight of these compounds is preferably in a range from about 56 to 280. If desired, up to 3 mol % of said compounds can be replaced by triols or triamines.

Diols i) which can be used are, for example, ethylene glycol, propylene glycol, butylene glycol, neopentyl glycol, cyclohexanedimethylol, di-, tri-, tetra-, penta- or hexaethylene glycol and mixtures thereof. Preference is given to using neopentyl glycol and/or cyclohexanedimethylol. Suitable aminoalcohols i) are, for example 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol etc. Suitable diamines i) are, for example, ethylenediamine, propylenediamine, 1,4-diaminobutane, 1,5-diaminopentane and 1,6-diaminohexane, and α,ω-diaminopolyethers, which can be prepared by amination of polyalkylene oxides with ammonia.

Component i) may also be a polymer with a number-average molecular weight in the range from about 300 to 5000, preferably about 400 to 4000, in particular 500 to 3000. Polymers i) which can be used are, for example, polyesterdiols, polyetherols and mixtures thereof. Polyetherols are preferably polyalkylene glycols, e.g. polyethylene glycols, polypropylene glycols, polytetrahydrofurans etc., block copolymers of ethylene oxide and propylene oxide or block copolymers of ethylene oxide, propylene oxide and butylene oxide which comprise the copolymerized alkylene oxide units in random distribution or in the form of blocks. Suitable polytetrahydrofurans i) can be prepared by cationic polymerization of tetrahydrofuran in the presence of acidic catalyst, such as, for example, sulfuric acid or fluorosulfuric acid. Such preparation processes are known to the person skilled in the art. Polyesterdiols i) which can be used preferably have a number-average molecular weight in the range from about 400 to 5000, preferably 500 to 3000, in particular 600 to 2000. Suitable polyesterdiols i) are all those which are customarily used for preparing polyurethanes, in particular those based on aromatic dicarboxylic acids, such as terephthalic acid, isophthalic acid, phthalic acid, Na or K sulfoisophthalic acid etc., aliphatic dicarboxylic acids, such as adipic acid or succinic acid etc., and cycloaliphatic dicarboxylic acids, such as 1,2-, 1,3- or 1,4-cyclohexanedicarboxylic acid. Suitable diols are, in particular, aliphatic diols, such as ethylene glycol, propylene glycol, 1,6-hexanediol, neopentyl glycol, diethylene glycol, polyethylene glycols, polypropylene glycols, 1,4-dimethylolcyclohexane, etc.

Suitable compounds II) which have two active hydrogen atoms and at least one carboxylic acid group per molecule are, for example, dimethylolpropanoic acid and mixtures which comprise dimethylolpropanoic acid.

Component iii) is a customary aliphatic, cycloaliphatic and/or aromatic polyisocyanate, such as tetramethylene diisocyanate, hexamethylene diisocyanate, methylene diphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof, in particular isophorone diisocyanate and/or dicyclohexylmethane diisocyanate. If desired, up to 3 mol % of said compounds can be replaced by triisocyanates.

Suitable additional polymers are also cationic polymers. These include, for example, polymers with the INCI name Polyquaternium, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamido copolymers (polyquaternium-7) and chitosan. Suitable cationic (quaternized) polymers are also Merquat® (polymer based on dimethyldiallylammonium chloride), Gafquat® (quaternary polymers which are formed by reacting polyvinylpyrrolidone with quaternary ammonium compounds), Polymer® JR (hydroxyethylcellulose with cationic groups) and cationic vegetable-based polymers, e.g. guar polymers, such as the Jaguar® grades from Rhodia.

Suitable additional polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and zwitterionic polymers which are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Neutral polymers suitable as additional polymers are, for example, polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic acid salts and derivatives. These include, for example, Luviflex® Swing (partially hydrolyzed copolymer of polyvinyl acetate and polyethylene glycol, BASF).

Suitable polymers are also nonionic, water-soluble or water-dispersible polymers or oligomers, such as polyvinylcaprolactam, e.g. Luviskole Plus (BASF), or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as are described, for example, in DE-A-43 33 238.

Suitable polymers are also nonionic, siloxane-containing, water-soluble or -dispersible polymers, e.g. polyethersiloxanes, such as Tegopren® (Goldschmidt) or Belsil® (Wacker).

The formulation base of pharmaceutical compositions according to the invention preferably comprises pharmaceutically acceptable auxiliaries. Pharmaceutically acceptable auxiliaries are auxiliaries which are known for use in the field of pharmacy, food technology and related fields, in particular those listed in the relevant pharmacopoeia (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirritatives, chelating agents, emulsion stabilizers, film formers, gel formers, odor-masking agents, resins, hydrocolloids, solvents, solubility promoters, neutralizing agents, permeation accelerators, pigments, quaternary ammonium compounds, regreasing and supergreasing agents, ointment, cream or oil base substances, silicone derivatives, stabilizers, sterilants, propellants, drying agents, opacifiers, thickeners, waxes, plasticizers, white oils. One embodiment in this respect is based on specialist knowledge, as represented, for example, in Fiedler, H. P. Lexikon der Hilfsstoffe für Pharmazie, Kosmetik und angrenzende Gebiete [Lexikon of auxiliaries for pharmacy, cosmetics and related fields], 4$^{th}$ edition, Aulendorf: ECV Editio-Kantor-Verlag, 1996.

To prepare the dermatological compositions according to the invention, the active ingredients can be mixed or diluted with a suitable auxiliary (excipient). Excipients may be solid, semisolid or liquid materials which can serve as a vehicle, carrier or medium for the active ingredient. The admixing of further auxiliaries takes place, if desired, in the manner known to the person skilled in the art. In addition, the polymers and polyelectrolyte complexes are suitable as auxiliaries in pharmacy, preferably as or in (a) coating(s) or binder(s) for solid drug forms. They can also be used in creams and as tablet coatings and tablet binders.

Pharmaceutical Preparations

One subject-matter of the invention relates to pharmaceutical compositions comprising the polymers according to the invention and pharmaceutically customary active ingredients and additives.

Solid pharmaceutical administration forms, such as tablets, capsules, pellets, granules, crystals etc., are coated, i.e.

provided with a film covering, for very different reasons. Thus, for example, a bad odor or taste can be masked, and the swallowability can be improved. The stability of the active ingredient can be increased as a result of the coating since less water vapor and oxygen passes to the inside of the tablet. The administration forms look better and can be better differentiated by incorporating dyes. Moreover, the release rate of the active ingredient can be adjusted in particular by virtue of the film coating.

In general, a distinction is made between instant release forms and slow-release forms. In the case of instant release forms, the disintegration of the tablet and the release of the active ingredient from the administration form should if possible not be influenced by the coating, and for this reason the film coating must dissolve rapidly in the gastric juice. In addition, it must have good film properties. The tensile strength and the elongation at break should be high so that the film coating withstands mechanical effects as arise during pharmaceutical processing—in particular formulation—and also during dispatch and/or storage.

One product which is frequently used for coating instant release tablets is hydroxypropylmethylcellulose (HPMC). Hydroxypropylmethylcellulose has a sharp viscosity increase in aqueous solution as the concentration increases. Similar behavior is also demonstrated by hydroxypropylcellulose (HPC).

Since the film former solution for the coating of tablets has to be finely atomized and the formed droplets must thoroughly wet the surface of the tablets and must also be readily sprayable, the viscosity should not exceed a certain limit (between 150 and 250 mPas), which is dependent on the type of spray nozzle and the instrument. For this reason, in the case of HPMC, only relatively low film former concentrations can be used.

The recommended concentration of Pharmacoat® 606 (Shin-etsu) stated in the literature is 5 to 7% by weight (Pharmaceutical Coating Technology, Ed. Graham Cole, Taylor and Francis Ltd. 1995 and technical datasheets from the manufacturer). These low spray concentrations lead to relatively long processing times and thus high costs.

Moreover, hydroxypropylmethylcellulose has further disadvantages, inter alia, with regard to wetting behavior, pigment-binding capacity, mechanical properties of the films, hygroscopicity, and permeability to water vapor and oxygen, dissolution rate and disintegration time difference between film tablets and core.

The low elasticity of the films made of hydroxypropylmethylcellulose often leads to the film tablets rupturing when stored in damp conditions as a result of the core swelling. Even the use of plasticizers does not result in noteworthy improvements of this problem. Instead, it can lead to sticky films and, as a result of migration, to changes in the properties of the tablets.

Oral drug forms with a release of medicament over a prolonged period with the aim of prolonging the effect of the active component (generally slow-release forms) are increasingly gaining importance. They are advantageously associated with improved patient compliance as a result of reduced taking frequency, a reduction in side effects through avoiding plasma peaks, more uniform level of the medicament in the blood, and the avoidance of local irritations. Besides the formulation of medicament-containing cores which have been coated with a water-insoluble but semipermeable or pore-containing film through which the medicament diffuses, the release can be controlled and prolonged by embedding the medicament into matrices. In addition, the use of ion exchanger resins and therapeutic systems (e.g. OROS) is possible.

The embedding of the medicament into hydrocolloids matrices in particular offers the advantages of simple and cost-effective preparation and high medicament safety since dose dumping effects cannot arise. The auxiliaries generally used here, such as hydroxypropylmethylcellulose (HPMC), hydroxypropylcellulose, alginic acid or alginates, and xanthan, have application disadvantages. These are: inadequate flow properties, which hinder direct tableting, dependency of the medicament release on the osmolarity (salt content) and on the pH of the release medium. This is true for HPMC as well as for hydroxypropylcellulose, xanthan and alginates. The use of xanthan also leads to tablets of lower hardness, the direct tableting of alginates results in compacts with only slight slow-release properties (max. 8 h). The natural swelling materials (e.g. alginates) have a high charge variability overall.

Binders are used in pharmaceutical administration forms in order to increase the processability and the mechanical strength. They are usually used in tablets, granules and pellets and lead to improved flowability, higher fracture resistance and lower friability.

The binders currently used, such as maltodextrin or polyvinylpyrrolidones, often lead to unsatisfactory fracture resistances and friabilities. Other binders, such as starch pastes and hydroxypropylmethylcellulose (HPMC) can only be used in low concentrations on account of their high viscosity.

In addition, film-forming auxiliaries are used in solutions and sprays which are applied to the skin or mucosa or else introduced systemically to the body. Examples thereof are preparations for the treatment of wounds, spray dressings, but also preparations for application to intact skin or mucosa. Here, the skin is protected by a film and the active ingredients can penetrate into and/or through the skin.

In the case of transdermal therapeutic systems and in the case of wound plasters, as in the case of the abovementioned administration forms, adequate flexibility is required which currently available products do not have. The use of possible plasticizers for achieving the necessary flexibility is undesired for toxicological and pharmacological reasons.

An object of the present invention was to provide water-soluble or water-dispersible polymers as coatings, binders and/or film formers in pharmaceutical preparations which do not have the disadvantages given above.

Surprisingly, it has been found that the polymers according to the invention are suitable for use in pharmaceutical preparations.

They are particularly suitable as coatings, binders, film formers and also as active ingredient release matrix in pharmaceutical preparations.

The polymers according to the invention can be used in a large number of pharmaceutical preparations.

Examples of coated preparations which may be mentioned are film tablets, film microtablets, sugar-coated tablets, coated pastilles, capsules, crystals, granules or pellets.

Binder-containing preparations are, for example, tablets, microtablets, cores, granules or pellets.

In addition, the polymers according to the invention can be used for the preparation of solutions and sprays which, applied to skin or mucosa, form a film.

Examples thereof are spray dressings for wounds, disinfection sprays, solutions with mycostatics, mouth sprays or lotions containing antibiotics etc. Use in transdermal therapeutic systems is also possible.

The polymers according to the invention readily wet lipophilic surfaces and have excellent protective colloid properties. When incorporated into suspensions and emulsions, they deposit themselves on the particles of the disperse phase and stabilize these. They can therefore be used as wetting auxiliaries and stabilizers in disperse systems.

As a result of interaction with sparingly water-soluble medicaments, they improve their solubility and dissolution rate, as a result of which resorbability and bioavailability of the medicaments are improved. This advantageous effect is evident, for example, with administration forms in which the active ingredient is not present in dissolved form, such as, for example, tablets, granules, suspensions etc.

The polymers according to the invention can, if appropriate, also in combination with other auxiliaries be processed together with active ingredients to give polymer-active ingredient melts which are either extruded and calendered to give medicaments or, following extrusion, are comminuted to give granules or powders and only then processed into drug forms, for example compressed to give tablets. Here, the polymers according to the invention introduce the properties already listed above into the preparations.

In different pharmaceutical preparations, the polymers according to the invention can fulfil the following functions in excellent manner:

dispersion auxiliary, suspension auxiliary, wetting agent, solubilizer for sparingly soluble medicaments, emulsifier, crystallization inhibitor, anticaking active ingredient, protective colloid, bioadhesive for prolonging and intensifying contact with the mucosa, spreading auxiliary, viscosity regulator, auxiliary for preparing solid solutions with medicaments, auxiliary for adjusting the active ingredient release in slow-release formulations.

The solubility of the polymers according to the invention can be adjusted within certain limits through suitable choice of the degree of neutralization. Thus, polymers according to the invention which are insoluble or only slightly soluble, but dispersible in water can also be used as slow-release polymers.

When used for producing suppositories and vaginal globuli, the polymers according to the invention ensure on the one hand the flexibility of the administration form and, on the other hand, promote disintegration and the dissolution of active ingredient and they coat the mucosa with an active-ingredient-containing film which enhances absorption.

Tablets swell to varying degrees depending on the auxiliaries and active ingredients used, the storage time and the storage conditions, such as temperature and humidity. A rigid film coating suffers cracks if the core swells. The elasticity of film formers is therefore an important parameter.

The polymers according to the invention, if appropriate neutralized, can be applied in pure form or else together with the customary auxiliaries to the active-ingredient-containing core. Customary auxiliaries are, for example, color pigments for coloring, white pigments, such as titanium dioxide, for increasing coverage, talc and silicon dioxide as detackifiers, polyethylene glycols, glycerol, propylene glycol, triacetin, triethyl citrate as plasticizer and various surface-active substances, such as sodium lauryl sulfate, polysorbate 80, pluronics and cremophors, for improving the wetting behavior. The substances specified by way of example do not represent any limitation. All known additives suitable for film coatings that are soluble in gastric juice can be used.

Coating methods which may be used are the customary methods, such as coating in a fluidized bed or a horizontal drum coater, and dip-coating and pan-coating methods. Besides the tablet application, the polymers according to the invention can also be used for coating other pharmaceutical preparations, such as granules, pellets, crystals or capsules. The novel coatings are applied in a conventional thickness of from 5 to 200 μm, preferably 10 to 100 μm.

When used as binders, a distinction is made between wet and dry binders depending on the processing method. The latter are used inter alia in direct tableting and in dry granulation or compaction. In these cases, the binder is mixed with the active ingredient and, if appropriate, further auxiliaries and then subjected to direct tableting, or granulation or compaction.

In contrast to this, for wet granulation, the active ingredient-auxiliary mixture is moistened with a solution of the binder in water or an organic solvent, and the moist mass is forced through a screen and then dried. The moistening and drying can also take place in parallel, as, for example, in fluidized-bed granulation.

For optimal processing, the binder should give low-viscosity solutions since viscous solutions lead to inhomogenous granules.

A binder should result in uniform, hard, abrasion-resistant granules or tablets. Fracture resistance is particularly important in particular for tablets because many active ingredients are difficult to compress and thus afford tablets with inadequate mechanical stability.

In addition, the disintegration of the drug forms, and the rate of release of the active ingredients should experience negligible adverse effects from the binder.

Examples of the most commonly used binders are polyvinylpyrrolidone, vinyl acetate/vinylpyrrolidone copolymers, gelatin, starch paste, maltodextrins, hydroxyalkylated and carboxyalkylated cellulose derivatives, such as hydroxypropylmethylcellulose, methylcellulose, sodiumcarboxymethylcellulose and types of natural gums, such as gum Arabic, pectin or alginate.

Many of these binders have a high viscosity in solution and are difficult to process. The high viscosity means that the powdered particles to be granulated are wetted poorly and unevenly, resulting in inadequate granule strength and an unfavorable particle size distribution.

Many binders are, moreover, hygroscopic and swell when water is absorbed. This may result in dramatic changes in the properties of granules and tablets.

Surprisingly, it has now been found that the sulfonated polymers comprising sulfone groups have excellent binding effects and, moreover, have a negligible effect on disintegration at concentrations in the range from 0.5 to 20% by weight, preferably 1 to 10% by weight, of the total amount of the formulation. On account of the good wetting characteristics, it is moreover possible for the release of active ingredients with poor solubility to be improved. The comparatively low viscosity of the polymer solutions should also be emphasized.

If required, the pharmaceutically acceptable additives and auxiliaries suitable for skin cosmetic and/or hair cosmetic preparations can of course be used in the pharmaceutical preparations.

When the polymers are used as binders, granules and tablets are obtained which have exceptional mechanical stability and are stable even over long storage periods.

A further preferred embodiment of the invention is skin-cleansing compositions.

Preferred skin-cleansing compositions are soaps of liquid to gel consistency, such as transparent soaps, luxury soaps, deodorant soaps, cream soaps, baby soaps, skin protection soaps, abrasive soaps and syndets, pasty soaps, lubricating soaps and washing pastes, liquid washing, showering and bathing preparations, such as washing lotions, shower baths and gels, foam baths, oil baths and scrub preparations, shaving foams, lotions and creams.

A further preferred embodiment of the invention is cosmetic compositions for the care and protection of the skin, nail care compositions or preparations for decorative cosmetics.

Suitable skin cosmetic compositions are, for example, face tonics, face masks, deodorants and other cosmetic lotions. Compositions for use in decorative cosmetics include, for example, concealing sticks, stage make-up, mascara and eyeshadows, lipsticks, kohl pencils, eyeliners, blushers, powders and eyebrow pencils.

In addition, the copolymers according to the invention can be used in nose strips for pore cleansing, in antiacne compositions, repellents, shaving compositions, hair-removal compositions, intimate care compositions, footcare compositions and in babycare.

The skin-care compositions according to the invention are, in particular, W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the copolymers according to the invention exhibit advantageous effects. The polymers can, inter alia, contribute to the moisturization and conditioning of the skin and to the improvement in the feel of the skin. The polymers can also act as thickeners in the formulations. The addition of the polymers according to the invention can achieve a considerable improvement in the skin compatibility in certain formulations.

Skin cosmetic and dermatological compositions preferably comprise at least one copolymer according to the invention in an amount of from about 0.001 to 30% by weight, preferably 0.01 to 20% by weight, very particularly preferably 0.1 to 12% by weight, based on the total weight of the composition.

Particularly photoprotective compositions based on the copolymers according to the invention have the property of increasing the residence time of the UV-absorbing ingredients compared with customary auxiliaries such as polyvinylpyrrolidone.

Depending on the field of use, the compositions according to the invention can be applied in a form suitable for skincare, such as, for example, in the form of a cream, foam, gel, stick, mousse, milk, spray (pumpspray or propellant-containing spray) or lotion.

Besides the copolymers according to the invention and suitable carriers, the skin cosmetic preparations can also comprise further active ingredients and auxiliaries customary in skin cosmetics, as described above. These include, preferably, emulsifiers, preservatives, perfume oils, cosmetic active ingredients, such as phytantriol, vitamin A, E and C, retinol, bisabolol, panthenol, photoprotective agents, bleaches, colorants, tints, tanning agents, collagen, protein hydrolyzates, stabilizers, pH regulators, dyes, salts, thickeners, gel formers, bodying agents, silicones, humectants, regreasing agents and further customary additives.

Preferred oil and fat components of the skin cosmetic and dermatological compositions are the abovementioned mineral and synthetic oils, such as, for example, paraffins, silicone oils and aliphatic hydrocarbons with more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof. The copolymers according to the invention can also be mixed with conventional polymers if specific properties are to be set.

To set certain properties, such as, for example, improvement in the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are prepared by customary methods known to the person skilled in the art.

Preferably, the cosmetic and dermatological compositions are in the form of emulsions, in particular in the form of water-in-oil (W/O) or oil-in-water (O/W) emulsions. It is, however, also possible to choose other types of formulations, for example hydrodispersions, gels, oils, oleogels, multiple emulsions, for example in the form of W/O/M, or O/W/O emulsions, anhydrous ointments and ointment bases, etc.

Emulsions are prepared by known methods. Besides at least one copolymer according to the invention, the emulsions generally comprise customary constituents, such as fatty alcohols, fatty acid esters and, in particular, fatty acid triglycerides, fatty acids, lanolin and derivatives thereof, natural or synthetic oils or waxes and emulsifiers in the presence of water. The selection of the additives specific to the type of emulsion and the preparation of suitable emulsions is described, for example, in Schrader, Grundlagen und Rezepturen der Kosmetika [Fundamentals and formulations of cosmetics], Hüthig Buch Verlag, Heidelberg, $2^{nd}$ edition, 1989, third part, which is hereby incorporated by reference.

A suitable emulsion, e.g. for a skin cream etc., generally comprises an aqueous phase which is emulsified by means of a suitable emulsifier system in an oil or fat phase. To prepare the aqueous phase, a copolymer according to the invention can be used.

Preferred fat components which can be present in the fat phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is about 250° C. and whose distillation end-point is at 410° C., such as, for example, vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglyce rides and cetyl ricinoleate.

The fatty phase can also comprise silicone oils soluble in other oils, such as dimethylpolysiloxane, methylphenylpolysiloxane and the silicone glycol copolymer, fatty acids and fatty alcohols.

Besides the copolymers according to the invention, waxes can also be used, such as, for example, carnauba wax, candilila wax, beeswax, microcrystalline wax, ozocerite wax and Ca, Mg and Al oleates, myristates, linoleates and stearates.

In addition, an emulsion according to the invention can be in the form of an O/N emulsion. Such an emulsion usually comprises an oil phase, emulsifiers which stabilize the oil phase in the water phase, and an aqueous phase which is usually in thickened form. Suitable emulsifiers are preferably O/W emulsifiers, such as polyglycerol esters, sorbitan esters or partially esterified glycerides.

According to a further preferred embodiment, the compositions according to the invention are a shower gel, a shampoo formulation or a bath preparation.

Such formulations comprise at least one copolymer according to the invention and usually anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickeners/gel formers, skin conditioners and humectants.

These formulations preferably comprise 2 to 50% by weight, preferably 5 to 40% by weight, particularly preferably 8 to 30% by weight of surfactants, based on the total weight of the formulation.

In the washing, showering and bathing preparations, all of the anionic, neutral, amphoteric or cationic surfactants customary in body-cleansing compositions can be used.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carbdxylates, alpha-olefin sulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 to 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or propionates, alkyl amphodiacetates or dipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mols per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

In addition, the washing, showering and bathing preparations can comprise customary cationic surfactants, such as, for example quaternary ammonium compounds, for example cetyltrimethylammonium chloride.

In addition, the shower gel/shampoo formulations can comprise thickeners, such as, for example, sodium chloride, PEG-55, propylene glycol oleate, PEG-120 methylglucose dioleate and others, and preservatives, further active ingredients and auxiliaries and water.

A particularly preferred embodiment of the invention is hair-treatment compositions.

Hair-treatment compositions according to the invention preferably comprise at least one copolymer according to the invention in an amount in the range from about 0.1 to 30% by weight, preferably 0.5 to 20% by weight, based on the total weight of the composition.

The hair-treatment compositions according to the invention are preferably in the form of a setting foam, hair mousse, hair gel, shampoo, hairspray, hair foam, end fluids, neutralizers for permanent waves, hair colorants and bleaches or "hot-oil treatments". Depending on the field of application, the hair cosmetic preparations can be applied in the form of an (aerosol) spray, (aerosol) foam, gel, gel spray, cream, lotion or wax. Hairsprays here comprise both aerosol sprays and also pump sprays without propellant gas. Hair foams comprise both aerosol foams and also pump foams without propellant gas. Hairsprays and hair foams preferably comprise predominantly or exclusively water-soluble or water-dispersible components. If the compounds used in the hairsprays and hair foams according to the invention are water-dispersible, they can be applied in the form of aqueous microdispersions with particle diameters of from usually 1 to 350 nm, preferably 1 to 250 nm. The solids contents of these preparations are here usually in a range from about 0.5 to 20% by weight. These microdispersions generally require no emulsifiers or surfactants for their stabilization.

The hair cosmetic formulations according to the invention comprise, in a preferred embodiment, a) 0.05 to 20% by weight of at least one copolymer according to the invention,
b) 20 to 99.95% by weight of water and/or alcohol,
c) 0 to 50% by weight of at least one propellant gas,
d) 0 to 5% by weight of at least one emulsifier,
e) 0 to 3% by weight of at least one thickener, and
f) up to 25% by weight of further constituents.

Alcohol is understood as meaning all alcohols customary in cosmetics, e.g. ethanol, isopropanol, n-propanol.

Further constituents are understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances, such as panthenol, collagen, vitamins, protein hydrolyzates, alpha- and beta-hydroxycarboxylic acids, protein hydrolyzates, stabilizers, pH regulators, dyes, viscosity regulators, gel formers, dyes, salts, humectants, regreasing agents, complexing agents and further customary additives.

All ingredients suitable for cosmetic compositions may, if appropriate, also be used for the hair cosmetic compositions.

These also include all styling and conditioning polymers known in cosmetics which can be used in combination with the polymers according to the invention if very specific properties are to be set.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and amino functional silicone compounds such as amodimethicones (CTFA).

The copolymers according to the invention are particularly suitable as setting agents in hairstyling preparations, in particular hairsprays (aerosol sprays and pump sprays without propellant gas) and hair foams (aerosol foams and pump foams without propellant gas).

In a preferred embodiment, spray preparations comprise
a) 0.1 to 10% by weight of at least one copolymer according to the invention,
b) 20 to 99.9% by weight of water and/or alcohol,
c) 0 to 70% by weight of at least one propellant,
d) 0 to 20% by weight of further constituents.

Propellants are the propellants customarily used for hairsprays and aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises
a) 0.1 to 10% by weight of at least one copolymer according to the invention,
b) 55 to 99.8% by weight of water and/or alcohol,
c) 5 to 20% by weight of a propellant,
d) 0.1 to 5% by weight of an emulsifier,
e) 0 to 10% by weight of further constituents.

Emulsifiers which can be used are all of the emulsifiers customarily used in hair foams. Suitable emulsifiers may be nonionic, cationic or anionic or amphoteric.

Propellants which are particularly suitable for aerosol foams are mixtures of dimethyl ether and if appropriate halogenated hydrocarbons, such as propane, butane, pentane or HFC-152 a.

Examples of nonionic emulsifiers (INCI nomenclature) are laureths, e.g. laureth-4; ceteths, e.g. cetheth-1, polyethylene glycol cetyl ether; ceteareths, e.g. cetheareth-25, polyglycol fatty acid glycerides, hydroxylated lecithin, lactyl esters of fatty acids, alkyl polyglycosides.

Examples of cationic emulsifiers are cetyidimethyl-2-hydroxyethylammonium dihydrogenphosphate, cetyltrimonium chloride, cetyltrimmonium bromide, cocotrimonium methyl sulfate, quaternium-1 to ×(INCI).

Anionic emulsifiers can, for example, be chosen from the group of alkyl sulfates, alkyl ether sulfates, alkylsulfonates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 and 3 ethylene oxide units, in the molecule.

A preparation suitable according to the invention for styling gels can, for example, have the following composition:
a) 0.1 to 10% by weight of at least one copolymer according to the invention,
b) 80 to 99.85% by weight of water and/or alcohol,
c) 0 to 3% by weight, preferably 0.05 to 2% by weight, of a gel former,
d) 0 to 20% by weight of further constituents.

The use of gel formers may, however, be advantageous for establishing specific rheological or other application properties of the gels. Gel formers which can be used are all gel formers customary in cosmetics. These include slightly crosslinked polyacrylic acid, for example Carbomer (INCI), cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, polyquaternium-32 (and) paraffinum liquidum (INCI), sodium acrylate copolymers (and) paraffinum liquidum (and) PPG-1 trideceth-6, acrylamidopropyltrimonium chloride/acrylamide copolymers, steareth-10 allyl ether acrylate copolymers, polyquaternium-37 (and) paraffinum liquidum (and) PPG-1-trideceth-6, polyquaternium 37 (and) propylene glycol dicaprate dicaprylate (and) PPG-1 trideceth-6, polyquaternium-7, polyquaternium-44.

The copolymers according to the invention can be used in cosmetic preparations as conditioners.

The copolymers according to the invention, as defined above, can preferably be used in shampoo formulations as setting and/or conditioning agents. Preferred shampoo formulations comprise
a) 0.05 to 10% by weight of at least one copolymer according to the invention,
b) 25 to 94.95% by weight of water,
c) 5 to 50% by weight of surfactants,
c) 0 to 5% by weight of a further conditioner,
d) 0 to 10% by weight of further cosmetic constituents.

In the shampoo formulations, all of the anionic, neutral, amphoteric or cationic surfactants used customarily in shampoos can be used.

Suitable anionic surfactants are, for example, alkyl sulfates, alkyl ether sulfates, alkylsulfonates, alkylarylsulfonates, alkyl succinates, alkyl sulfosuccinates, N-alkoyl sarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 and 3 ethylene oxide units, in the molecule.

Examples of suitable compounds are sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzene-sulfonate, triethanolamine dodecylbenzenesulfonate.

Suitable amphoteric surfactants are, for example, alkylbetaines, alkylamidopropyl-betaines, alkylsulfobetaines, alkyl glycinates, alkyl carboxyglycinates, alkyl amphoacetates or amphopropionates, alkylamphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mols per mole of alcohol. In addition, alkylamine oxides, mono- or dialkylalkanolamides, fatty acid esters of polyethylene glycols, alkyl polyglycosides or sorbitan ether esters are suitable.

Furthermore, the shampoo formulations can comprise customary cationic surfactants, such as, for example, quaternary ammonium compounds, for example cetyltrimethylammonium chloride.

In the shampoo formulations, conditioners customary for achieving certain effects can be used in combination with the copolymers according to the invention. These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamide copolymers (polyquaternium-7). It is also possible to use protein hydrolyzates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and amino functional silicone compounds, such as amodimethicones (CTFA). Cationic guar derivatives such as guarhydroxypropyl-trimonium chloride (INCI) can also be used.

The invention further provides the use of a copolymer, as defined above, as auxiliary in pharmacy, preferably as or in (a) coating(s) for solid drug forms, for modifying rheological properties, as surface-active compound, as or in (an) adhesive(s), and as or in (a) coating(s) for the textile, paper, printing and leather industry.

The invention is explained in more detail with reference to the following nonlimiting examples.

EXAMPLES

Abbreviations Used Below

EMA Ethyl methacrylate
MAM Methacrylamide
MM Methacrylic acid
M Acrylic acid
DMAPMAM N-[3-(dimethylamino)propyl]methacrylamide
NtBAM N-tert-Butylacrylamide
NtBAEMA N-(tert-Butyl)aminoethyl methacrylate
VI Vinylimidazole
TEA Triethanolamine General preparation procedure: solution polymerization in ethanol/water (2:1)

Example No. 17

Preparation of 500 g of a 30% strength by weight ethanol/water [2.1:1] solution of a polymer of the composition EMA/MAM/MAS/AS/NtBAEMA 65/7/22/3/3

| Initial charge | 27 g | water |
| | 40 g | ethanol |
| | 16.6 g | feed 1 |
| | 0.85 g | feed 2 |

-continued

| Feed 1: | 97.5 g | ethyl methacrylate | 70.0 methacrylamide 15% by we |
| | 33.0 g | methacrylic acid | |
| | 4.5 g | acrylic acid | |
| | 4.5 g | N-tert-butylaminoethyl methacrylate | |
| | 122.5 g | ethanol | |
| Feed 2 | 3.0 g | Waco ® V50 | |
| | 14 g | water | |
| Feed 3 | 0.75 g | tert-butyl perpivalate 75% strength | |
| | 43.75 g | ethanol | |
| Feed 4 | 37.75 g | aminomethylpropanol AMP | |
| | 25.15 g | water | |
| | 105 g | ethanol | |

In a stirred apparatus with reflux condenser, internal thermometer and four separate feed devices, 16.6 g of feed 1, 0.85 of feed 2, 27 g of water and 40 g of ethanol were initially introduced and the mixture was heated to about 65° C. with stirring. After the onset of polymerization, evident from a slight increase in viscosity, the remainder of feed 1 was added over the course of three hours and the remainder of feed 2 was added over the course of 4 hours at 67° C. The reaction solution was after-stirred for about a further two hours at 70° C. Feed 3 was metered in at about 70° C. over 30 minutes. The polymer mixture was after-polymerized for about a further two hours at 80° C. The polymer solution was neutralized with AMP in feed 4 over 10 minutes. This gave 500 g of an approximately 30% strength by weight of aqueous-ethanolic polymer solution.

The polymers of Examples 1 to 20 below were prepared in the same way.

The amounts given for the monomers are in % by weight.

| Ex. No. | EMA | MAM | NtBAM | MAA | AA | NtBA-EMA | VI | DMAP-MAM | Neutralizing agent/degree of neutralization [%] |
|---|---|---|---|---|---|---|---|---|---|
| 1 | 55 | — | 20 | 25 | — | — | — | — | AMP/80-TEA/20* |
| 2 | 50 | — | 25 | 25 | — | — | — | — | AMP/100 |
| 3 | 65 | — | 10 | 20 | 5 | — | — | — | AMP/100 |
| 4 | 68 | — | 10 | 17 | 5 | — | — | — | AMP/100 |
| 5 | 70 | 10 | — | 17 | 3 | — | — | — | AMP/100 |
| 6 | 68 | 10 | — | 17 | 5 | — | — | — | AMP/100 |
| 7 | 68 | 10 | — | 15 | 7 | — | — | — | AMP/100 |
| 8 | 60 | 15 | — | 20 | 5 | — | — | — | AMP/100 |
| 9 | 65 | 10 | — | 22 | 3 | — | — | — | AMP/100 |
| 10 | 70 | 5 | — | 22 | 3 | — | — | — | AMP/100 |
| 11 | 70 | 5 | — | 25 | — | — | — | — | AMP/50-TEA/50* |
| 12 | 70 | 5 | — | 22 | 3 | — | — | — | AMP/100 |
| 13 | 60 | 10 | — | 25 | 5 | — | — | — | AMP/100 |
| 14 | 55 | 10 | — | 25 | 10 | — | — | — | AMP/100 |
| 15 | 60 | — | 12 | 25 | — | 3 | — | — | AMP/100 |
| 16 | 60 | — | 12 | 25 | — | — | 3 | — | AMP/100 |
| 17 | 65 | 7 | — | 22 | 3 | 3 | — | — | AMP/100 |
| 18 | 65 | 7 | — | 22 | 3 | — | 3 | — | AMP/100 |
| 19 | 65 | 10 | — | 22 | — | — | — | 3 | AMP/50-TEA/50* |
| 20 | 65 | — | 10 | 20 | — | — | — | 3 | AMP/50-TEA/50' |

*100% neutralization is achieved by 80 + 20 or 50 + 50 neutralization by combining the two neutralizing agents AMP and TEA.

Determination of the K Value:

The K values were measured in accordance with Fikentscher, *Cellulosechemie*, Vol. 13, pp. 58 to 64 (1932) at 25° C. in aqueous/ethanolic or ethanolic solution and represent a measure of the molar weight. The aqueous/ethanolic or ethanolic solution of the polymers comprises 1 g of polymer in 100 ml of solution. When the polymers are in the form of aqueous dispersions, appropriate amounts of the dispersion depending on the polymer content of the dispersion are topped up to 100 ml with ethanol so that the concentration of 1 g of polymer in 100 ml of solution arise.

The K value was measured in a Micro-Ubbelohde capillary type M Ic from Schott.

Determination of the Flexural Rigidity:

To measure the flexural rigidity, 3.0% strength by weight solutions of the polymers according to the invention are prepared.

The flexural rigidity measurement is carried out on 5 to 10 hair tresses (each about 3 g and 24 cm in length) at 20° C. and a relative humidity of 65%.

The weighed, dry hair tresses were dipped into the 3% strength polymer solution, uniform distribution being ensured by immersion and removal three times.

The excess film former solution is stripped off between thumb and forefinger and the hair tresses are then carefully squeezed by squeezing between filter paper. The tresses are then shaped by hand to give a round cross section. They are dried overnight in a climatically controlled room at 20° C. and a relative humidity of 65%. The experiments were carried out in a climatically controlled room at 20° C. and a relative humidity of 65% by means of a tension/compression testing device.

The hair tress is placed symmetrically on two cylindrical rolls of the sample holder. The tress is then bent exactly in the middle from above using a rounded punch by 40 mm (breakage of the polymer film). The force required for this is measured using a weighing cell (50 N) and given in Newtons.

| Example No. | EMA | MAM | N$^r$BAM | MAA | AA | DMAP MAM | K value | Flexural rigidity [cN] |
|---|---|---|---|---|---|---|---|---|
| 6 | 68 | 10 | — | 17 | 5 | — | 38.5 | 400 cN |
| 7 | 68 | 10 | — | 15 | 7 | — | 42.2 | 370 cN |

Application Examples

Example 1

| VOC 80 aerosol hairspray | % by weight |
|---|---|
| Polymer from Example No. 1 | 12.00 |
| (30% strength aqueous-ethanolic dispersion) | |
| Water | 13.60 |
| Dimethyl ether | 40.00 |
| Ethanol | 34.40 |
| Further additive: silicone, perfume, antifoam . . . | |

The example can be repeated with the polymers of Examples 2-4 and 10-20. In each case, a VOC 80 aerosol hairspray with good properties is obtained.

Example 2

| VOC 80 aerosol hairspray | % by weight |
|---|---|
| Polymer from Example No. 1 | 12.00 |
| (30% strength aqueous-ethanolic dispersion) | |
| Luvimer ®100P | 1.0 |
| Water | 12.20 |
| Dimethyl ether | 40.00 |
| Ethanol | 34.40 |
| Aminomethylpropanol (95% strength) | 0.40 |
| Further additive: silicone, perfume, antifoam . . . | |

The example can be repeated with the polymers of Examples 2 to 20. In each case, a VOC 80 aerosol hairspray with good properties is obtained.

Example 3

| VOC 55 aerosol hairspray | % by weight |
|---|---|
| Polymer from Example No. 1 | 15.00 |
| (30% strength aqueous-ethanolic dispersion) | |
| Water | 37.00 |
| Dimethyl ether | 40.00 |
| Ethanol | 8.00 |
| Further additive: silicone, perfume, antifoam . . . | |

The example can be repeated with the polymers of Examples 2 to 20. In each case, a VOC 55 aerosol hairspray with good properties is obtained.

Example 4

| VOC 55 aerosol hairspray | % by weight |
|---|---|
| Polymer from Example No. 1 | 12.00 |
| (30% strength aqueous-ethanolic dispersion) | |
| Luviset ® P.U.R. (30% strength aqueous-ethanolic dispersion) | 3.00 |
| Water | 35.90 |
| Dimethyl ether | 40.00 |
| Ethanol | 9.10 |
| Further additive: silicone, perfume, antifoam . . . | |

The example can be repeated with the polymers of Examples 2 to 20. In each case, a VOC 55 aerosol hairspray with good properties is obtained.

Example 5

| VOC 55 aerosol hairspray | % by weight |
| --- | --- |
| Polymer from Example No. 1 | 12.00 |
| (30% strength aqueous-ethanolic dispersion) | |
| Luvimer ® Pro55 (30% strength dispersion) | 3.00 |
| Water | 35.90 |
| Dimethyl ether | 40.00 |
| Ethanol | 8.80 |
| Aminomethylpropanol (95% strength) | 0.30 |
| Further additive: silicone, perfume, antifoam . . . | |

The example can be repeated with the polymers of Examples 2 to 20. In each case, a VOC 55 aerosol hairspray with good properties is obtained.

Example 6

| VOC 55 aerosol hairspray | % by weight |
| --- | --- |
| Polymer from Example No. 1 | 12.00 |
| (30% strength aqueous-ethanolic dispersion) | |
| Stepanhold ® R-1 *⁾ (Stepan Chemical Co.) | 1.00 |
| Water | 37.40 |
| Dimethyl ether | 40.00 |
| Ethanol | 9.40 |
| Aminomethylpropanol (95% strength) | 0.20 |
| Further additive: silicone, perfume, antifoam . . . | |

*⁾ Stepanhold R-1 = poly(vinylpyrrolidone/ethyl methacrylate/methacrylic acid)

The example can be repeated with the polymers of Examples 2 to 20. In each case, a VOC 55 aerosol hairspray with good properties is obtained.

Example 7

| VOC 55 pump spray | % by weight |
| --- | --- |
| Polymer from Example No. 1 | 15.00 |
| (30% strength aqueous-ethanolic dispersion) | |
| Water | 37.00 |
| Ethanol | 48.00 |
| Further additive: silicone, perfume, antifoam . . . | |

The example can be repeated with the polymers of Examples 2 to 20. In each case, a VOC 55 pump spray with good properties is obtained.

Example 8

| VOC 55 pump spray | % by weight |
| --- | --- |
| Polymer from Example No. 1 | 12.00 |
| (30% strength aqueous-ethanolic dispersion) | |
| Luviset ® Clear *⁾ (BASF AG) 20% strength | 5.00 |
| Water | 33.60 |
| Ethanol | 49.40 |
| Further additive: silicone, perfume, antifoam . . . | |

*⁾ Luviset ® Clear = poly(vinylpyrrolidone/methacrylamide/vinylimidazole)#

The example can be repeated with the polymers of Examples 2 to 20. In each case, a VOC 55 pump spray with good properties is obtained.

Example 9

| VOC <10 pump spray | % by weight |
| --- | --- |
| Polymer from Example No. 1 | 12.00 |
| (30% strength aqueous ethanolic dispersion) | |
| Luviset ® Clear *⁾ (BASF AG) 20% strength | 5.00 |
| Water | 83.00 |
| Further additive: silicone, perfume, antifoam . . . | |

*⁾ Luviset ® Clear = poly(vinylpyrrolidone/methacrylamide/vinylimidazole)

The example can be repeated with the polymers of Examples 2 to 20. In each case, a VOC 55 pump spray with good properties is obtained.

Example 10

| Setting foam | % by weight |
| --- | --- |
| Polymer from Example No. 1 | 10.00 |
| (30% strength aqueous-ethanolic dispersion) | |
| Luviset ® Clear *⁾ (BASF AG) 20% strength | 5.00 |
| Cremophor ®A 25 (Ceteareth 25/BASF) | 0.20 |
| Comperlan ®KD (Coamide DEA/Henkel) | 0.10 |
| Water | 74.70 |
| Propane/butane | 10.00 |
| Further additive: perfume, preservative . . . | |

Preparation: weigh in and dissolve with stirring. Bottle and add propellant gas.

The example can be repeated with the polymers of Examples 2 to 20. In each case, a VOC 55 pump spray with good properties is obtained.

Example 11

| Hair gel containing Aculyn ® 28: | % by weight |
| --- | --- |
| Phase 1: | |
| Polymer from Example No. 1 | 12.00 |
| (30% strength aqueous-ethanolic dispersion) | |
| Water, dist. | 37.00 |
| Aminomethylpropanol (38% strength solution) | 1.0 |
| Further additive: preservative, soluble ethoxylated silicone, perfume . . . | |
| Phase 2: | |
| Aculyn ® 28 (1% strength aqueous suspension) | 50.00 |

Preparation: phases 1 and 2 are weighed in and homogenized separately. Phase 2 is then slowly stirred into phase 1. An almost clear, stable gel is formed.

The example can be repeated with the polymers of Examples 2 to 20. In each case, a hair gel containing Aculyn 28 with good properties is obtained.

Example 12

| Hair gel containing hydroxyethylcellulose | % by weight |
|---|---|
| Phase 1: | |
| Polymer from Example No. 1 (30% strength aqueous-ethanolic dispersion) | 12.00 |
| Water, dist. | 38.00 |
| Further additive: preservative, soluble ethoxylated silicone, perfume . . . | |
| Phase 2: | |
| Natrosol ® HR 250 (5% strength solution) Hydroxyethylcellulose (Hercules) | 50.00 |

Preparation:
Phases 1 and 2 are weighed in and homogenized separately. Phase 2 is then slowly stirred into phase 1. An essentially clear, stable gel is formed.

The example can be repeated with the polymers of Examples 2 to 20. In each case, a hair gel containing hydroxyethylcellulose with good properties is obtained.

Example 13

| Conditioner shampoo | % by weight |
|---|---|
| A) Texapon ® NSO 28% strength (sodium laureth sulfate/Henkel) | 50.00 |
| Comperlan ® KS (Coamide DEA/Henkel) | 1.00 |
| Polymer from Example No. 14 (30% strength aqueous-ethanolic dispersion) | 12.00 |
| q.s. perfume oil | |
| B) Water | 27.5 |
| Sodium chloride | 1.5 |
| q.s. preservative . . . | |

Preparation:
Phases 1 and 2 are weighed in and homogenized separately. Phase 2 is then slowly stirred into phase 1. An essentially clear, stable gel is formed.

The example can be repeated with the polymers of Examples 15 to 20. In each case, a conditioner shampoo with good properties is obtained.

Example 14

| Standard O/W cream: | | |
|---|---|---|
| % by weight | | CTFA name |
| Oil phase: | | |
| Cremophor ® A6 | 3.5 | Ceteareth-6 (and) Stearyl Alcohol |
| Cremophor ®A25 | 3.5 | Ceteareth-25 |
| Glycerol monostearate s.e. | 2.5 | Glyceryl Stearate |
| Paraffin oil | 7.5 | Paraffin Oil |
| Cetyl alcohol | 2.5 | Cetyl Alcohol |
| Luvitol ®EHO | 3.2 | Cetearyl Octanoate |
| Vitamin E acetate | 1.0 | Tocopheryl Acetate |
| Nip-nip | 0.1 | Methyl and Propyl 4-hydroxybenzoate (7:3) |

-continued

| Standard O/W cream: | | |
|---|---|---|
| % by weight | | CTFA name |
| Water phase: | | |
| Polymer from Example No. 14 (30% strength aqueous ethanol dispersion) | 3.0 | |
| Water | 71.6 | |
| 1,2-Propylene glycol | 1.5 | Propylene Glycol |
| Germall ® II | 0.1 | Imidazolidinyl Urea |

Preparation:
The oil and water phases are weighed in separately and homogenized at a temperature of about 80° C. The water phase is then slowly stirred into the oil phase and slowly cooled to room temperature with stirring.

The example can be repeated with the polymers of Examples 15 to 20. In each case, a standard O/W cream with good properties is obtained.

Unless described otherwise, the quantities of the individual components given below are always in % by weight.

Example 15

Sun Screen Gel

| % by weight | |
|---|---|
| Phase A | |
| 1.00 | Hydrogenated castor oil PEG-40 |
| 8.00 | Octyl methoxy cinnamate (Uvinul ®MC 80 from BASF) |
| 5.00 | Octocrylene (Uvinul ®N 539 from BASF) |
| 0.80 | Octyl triazone (Uvinul ®T 150 from BASF) |
| 2.00 | Butylmethoxydibenzoylmethane (Uvinul ®BMBM from BASF) |
| 2.00 | Tocopheryl acetate |
| q.s. | Perfume oil |
| Phase B | |
| 10.00 | Polymer 1 (30% strength aqueous-ethanol dispersion) |
| 0.30 | Acrylate/$C_{10-30}$ alkyl acrylate copolymer |
| 0.20 | Carbomer |
| 5.00 | Glycerol |
| 0.20 | Disodium EDTA |
| q.s. | Preservative |
| 65.30 | dist. water |
| Phase C | |
| 0.20 | Sodium hydroxide |

Preparation:
Mix the components of phase A. Allow phase B to swell and stir into phase A with homogenization. Neutralize with phase C and homogenize again.

The example can be repeated with the polymers of Examples 2 to 20. In each case, a sunscreen gel with good properties is obtained.

Example 16

| Body lotion foam | |
|---|---|
| Phase A | |
| 1.50 | Ceteareth-25 |
| 1.50 | Ceteareth-6 |
| 4.00 | Cetearyl alcohol |

-continued

Body lotion foam

| 10.00 | Cetearyl octanoate |
| 1.00 | Dimethicone |

Phase B

| 3.00 | Polymer 1 (30% strength aqueous-ethanol. dispersion) |
| 2.00 | Panthenol |
| 2.50 | Propylene glycol |
| q.s. | Preservative |
| 74.50 | dist. water |

Phase C

| q.s. | Perfume oil |

Preparation:
Heat phase A and B separately to about 80° C. Stir phase B into phase A and homogenize. Cool to about 40° C., add phase C and briefly homogenize again. Bottling: 90% active ingredient and 10% propane/butane at 3.5 bar (20° C.).

The example can be repeated with the polymers of Examples 2 to 7. In each case, a body lotion foam with good properties is obtained.

Example 17

Shaving Foam

| 6.00 | Ceteareth-25 |
| 5.00 | Poloxamer 407 |
| 52.00 | dist. water |
| 1.00 | Triethanolamine |
| 5.00 | Propylene glycol |
| 1.00 | Lanolin oil PEG-75 |
| 5.00 | Polymer 1 according to the invention (30% strength aqueous-ethanol. dispersion) |
| q.s. | Preservative |
| q.s. | Perfume oil |
| 25.00 | Sodium laureth sulfate |

Preparation:
Weigh everything together, then stir until dissolved. Bottling: 90 parts of active substance and 10 parts of propane/butane 25:75 mixture.

The example can be repeated using the polymers of Examples 2 to 20. In each case, a shaving foam with good properties is obtained.

Preparation:
Dissolve phase A. Sprinkle phase B into phase A and dissolve. Add phase C and leave to stir under reduced pressure at RT for about 45 min.

The example can be repeated with the polymers of Examples 2 to 7. In each case, a toothpaste with good properties is obtained.

Example 18b

Shower Gel

| 50.00 | Sodium laureth sulfate, magnesium laureth sulfate, sodium laureth-8 sulfate, magnesium laureth-8 |
| 1.00 | Cocoamide DEA |
| 4.00 | Polymer 1 (30% strength aqueous-ethanol. dispersion) |
| 2.00 | Sodium laureth sulfate, glycol distearate, cocamide MEA, laureth-10 |
| q.s. | Preservative |
| q.s. | Perfume oil |
| 2.00 | Sodium chloride |
| 41.00 | dist. water |

Preparation:
Weigh in all of the components together and stir until dissolved.

The example can be repeated with the polymers of Examples 2 to 7. In each case, a shower gel with good properties is obtained.

Example 18b

Shower Gel

| 30.00 | Sodium laureth sulfate |
| 6.00 | Sodium cocoamphodiacetate |
| 6.00 | Cocamidopropylbetaine |
| 3.00 | Sodium laureth sulfate, glycol distearate, cocamide MEA, laureth-10 |
| 7.70 | Polyquaternium-44 |
| 1.50 | Polymer 1 (25% strength aqueous dispersion) |
| 1.00 | Panthenol |
| q.s. | Preservative |
| q.s. | Perfume oil |
| q.s. | Citric acid |
| 0.50 | Sodium chloride |
| 44.30 | dist. water |

Preparation:
Weigh in the components of phase A and dissolve. Adjust the pH to 6 to 7.

The example can be repeated with the polymers of Examples 2 to 7. In each case, a shower gel with good properties is obtained.

Example 19

Clear Shower Gel

| 40.00 | Sodium laureth sulfate |
| 5.00 | Decyl glucoside |
| 5.00 | Cocamidopropylbetaine |
| 0.50 | Polyquaternium-10 |
| 8.00 | Polymer 1 (30% strength aqueous-ethanol. dispersion) |
| 1.00 | Panthenol |
| q.s. | Perfume oil |
| q.s. | Preservative |
| q.s. | Citric acid |
| 2.00 | Sodium chloride |
| 38.50 | dist. water |

Preparation:
Weigh in the components of phase A and dissolve to give a clear solution.

The example can be repeated with the polymers of Examples 2 to 20. In each case, a clear shower gel with good properties is obtained.

Example 20

Shower Bath

A

| 40.00 | Sodium laureth sulfate |
| 5.00 | Sodium $C_{12-15}$ pareth-15 sulfonate |

-continued

| | |
|---|---|
| 5.00 | Decyl glucoside |
| q.s. | Perfume oil |
| 0.10 | Phytantriol |

B

| | |
|---|---|
| 35.80 | Dist. water |
| 0.1 | Guar hydroxypropyltrimonium chloride |
| 10.00 | Polymer 1 (30% strength aqueous-ethanol. dispersion) |
| 1.00 | Panthenol |
| q.s. | Preservative |
| 1.00 | Laureth-3 |
| q.s. | Citric acid |
| 2.00 | Sodium chloride |

Preparation:
Mix the components of phase A. Add the components of phase B one after the other and mix. Adjust the pH to 6 to 7.

The example can be repeated with the polymers of Examples 2 to 20. In each case, a shower bath with good properties is obtained.

Example 21

Liquid Soap

A

| | |
|---|---|
| 43.26 | Dist. water |
| 0.34 | Aminomethylpropanol |
| 3.40 | Poly(ethyl acrylate/methacrylic acid) (Luviflex ®Soft, BASF) |

B

| | |
|---|---|
| 40.00 | Sodium laureth sulfate |
| 10.00 | Cocamidopropylbetaine |
| 1.00 | Polymer 1 (20% strength aqueous dispersion) |
| q.s. | Perfume oil |
| q.s. | Preservative |
| 2.00 | Sodium chloride |

Preparation:
Weigh in the components of phase A and dissolve until clear. Add the components of phase B one after the other and mix.

The example can be repeated with the polymers of Examples 2 to 20. In each case, a liquid soap with good properties is obtained.

Example 22

Freshening Gel

A

| | |
|---|---|
| 0.60 | Carbomer |
| 45.40 | Dist. water |

B

| | |
|---|---|
| 0.50 | Bisabolol |
| 0.50 | Farnesol |
| q.s. | Perfume oil |
| 5.00 | PEG-40 hydrogenated castor oil |
| 2.50 | Polymer 1 (30% strength aqueous-ethanol. dispersion) |
| 1.00 | Tetrahydroxypropylethylenediamine |
| 1.50 | Menthol |
| 43.00 | Alcohol |
| q.s. | C.I. 74 180, Direct Blue 86 |

Preparation:
Allow phase A to swell. Dissolve phase B. Stir phase B into phase A.

The example can be repeated with the polymers of Examples 2 to 20. In each case, a freshening gel with good properties is obtained.

Example 23

Aerosol Hair Foam

A

| | |
|---|---|
| 2.00 | Cocotrimonium methosulfate |
| 0.20 | Perfume oil |

B

| | |
|---|---|
| 64.40 | Dist. water |
| 6.70 | Polymer 1 (25% strength aqueous dispersion) |
| 0.50 | Poly(ethyl acrylate/methacrylic acid) (Luviflex ®Soft, BASF) |
| 0.10 | Aminomethylpropanol |
| 0.20 | Ceteareth-25 |
| 0.20 | Trimethylsilylamodimethicone, Trideceth-10, cetrimonium chloride |
| 0.10 | PEG-25 PABA |
| 0.20 | Hydroxyethylcellulose |
| 0.20 | PEG-8 |
| 0.20 | Panthenol |
| 15.00 | Alcohol |

C

| | |
|---|---|
| 10.00 | Propane/butane 3.5 bar (20° C.) |

Preparation:
Mix phases A and B and bottle with propellant gas.

The example can be repeated with the polymers of Examples 2 to 20. In each case, an aerosol hair foam with good properties is obtained.

Example 24

Pump Mousse

A

| | |
|---|---|
| 2.00 | Cocotrimonium methosulfate |
| q.s. | Perfume oil |

C

| | |
|---|---|
| 74.30 | Dist. water |
| 7.00 | Polyquaternium-46 (10% strength aqueous solution) |
| 15.00 | Polymer 1 (20% strength aqueous dispersion) |
| 0.50 | PEG-8 |
| 1.00 | Panthenol |
| q.s. | Preservative |
| 0.20 | PEG-25 PABA (ethoxylated p-aminobenzoic acid) |

Preparation:
Mix the components of phase A. Add the components of phase B one after the other and dissolve to give a clear solution.

The example can be repeated with the polymers of Examples 2 to 7. In each case, a pump mousse with good properties is obtained.

Example 25

Aerosol Foam

| | |
|---|---|
| 10.00 | Polymer 1 (30% strength aqueous-ethanol. dispersion) |
| 5.00 | PVP/VA copolymer (40% strength aqueous solution) |
| 0.50 | Hydroxyethylcetyldimonium phosphate |
| 0.20 | Ceteareth-25 |

-continued

| | |
|---|---|
| 0.40 | Perfume oil PC 910.781/cremophor |
| 73.90 | Dist. water |
| q.s. | Preservative |
| 10.00 | Propane/butane 3.5 bar (20° C.) |

Preparation:
Weigh everything together, stir until dissolved, then bottle.

The example can be repeated with the polymers of Examples 2 to 20. In each case, an aerosol foam with good properties is obtained.

Example 26

Color Styling Mousse

| | |
|---|---|
| A | |
| 2.00 | Cocotrimonium methosulfate |
| q.s. | Perfume oil |
| B | |
| 20.00 | Polymer 1 (30% strength aqueous-ethanol. dispersion) |
| 0.50 | Acrylatecopolymer (Luvimer ®100 P, BASF) |
| 0.10 | Aminomethylpropanol |
| 0.20 | Ceteareth-25 |
| 0.20 | Panthenol |
| 0.20 | Hydroxyethylcellulose |
| 10.00 | Alcohol |
| 56.67 | Dist. water |
| 0.08 | C.I. 12245, Basic Red 76 |
| 0.05 | C.I. 42510, Basic Violet 14 |
| C | |
| 10.00 | Propane/butane 3.5 bar (20° C.) |

Preparation:
Weigh everything together, stir until dissolved, then bottle. Only suitable for dark blond and brown hair!

The example can be repeated with the polymers of Examples 2 to 20. In each case, a color styling mousse with good properties is obtained.

Example 27

Pump Hair Foam

| | |
|---|---|
| A | |
| 1.50 | Cocotrimoniummethosulfate |
| q.s. | Perfume oil |
| B | |
| 10.00 | Polymer 1 (20% strength aqueous dispersion) |
| 84.04 | Dist. water |
| C | |
| 0.46 | Aminomethylpropanol |
| 4.00 | PEG/PPG-25/25 dimethicone/acrylate copolymer |
| q.s. | Preservative |

Preparation:
Mix phase A. Stir phase B into phase A. Add phase C and stir until dissolved.

The example can be repeated with the polymers of Examples 2 to 20. In each case, a pump hair foam with good properties is obtained.

Example 28

Aquawax

| | |
|---|---|
| 50.00 | Polymer 1 (20% strength aqueous dispersion) |
| q.s. | Perfume oil |
| q.s. | Hydrogenated castor oil PEG-40 |
| 0.10 | Diethyl phthalate |
| 0.10 | Cetearylethyl hexanoate |
| 0.10 | PEG-7 glyceryl cocoate |
| 0.10 | Preservative |
| 47.60 | Dist. water |
| 2.00 | Caprylic/capric triglyceride, acrylate copolymer |

Preparation:
Mix everything and homogenize. After-stir for 15 minutes.

The example can be repeated with the polymers of Examples 2 to 20. In each case, an aquawax with good properties is obtained.

Example 29

Shampoo

| | |
|---|---|
| 30.00 | Sodium laureth sulfate |
| 6.00 | Sodium cocoamphoacetate |
| 6.00 | Cocamidopropylbetaine |
| 3.00 | Sodium laureth sulfate, glycol distearate, cocamide MEA, Laureth-10 |
| 3.00 | Polymer 1 (30% strength aqueous-ethanol. dispersion) |
| 2.00 | Dimethicone |
| q.s. | Perfume |
| q.s. | Preservative |
| q.s. | Citric acid |
| 1.00 | Sodium chloride |
| ad 100 | Dist. water |

Preparation:
Weigh in components and dissolve. Adjust pH to 6 to 7.

The example can be repeated with the polymers of Examples 2 to 20. In each case, a shampoo with good properties is obtained.

Example 30

Antidandruff Shampoo

| | |
|---|---|
| 40.00 | Sodium laureth sulfate |
| 10.00 | Cocamidopropylbetaine |
| 10.00 | Disodium laureth sulfosuccinate |
| 2.50 | Sodium laureth sulfate, glycol distearate, cocamide MEA, Laureth-10 |
| 3.00 | Polymer 1 (30% strength aqueous-ethanol. dispersion) |
| 0.50 | Climbazole |
| q.s. | Perfume |
| q.s. | Preservative |
| 0.50 | Sodium chloride |
| ad 100 | Dist. water |

Preparation:
Weigh in components and dissolve. Adjust pH to 6 to 7.

The example can be repeated with the polymers of Examples 2 to 20. In each case, an antidandruff shampoo with good properties is obtained.

Example 31

Clear Shower Gel

| | |
|---|---|
| 40.00 | Sodium laureth sulfate |
| 5.00 | Decyl glucoside |
| 5.00 | Cocamidopropylbetaine |
| 3.00 | Polymer 1 (30% strength aqueous-ethanol. dispersion) |
| 1.00 | Panthenol |
| q.s. | Perfume |
| q.s. | Preservative |
| q.s. | Citric acid |
| 2.00 | Sodium chloride |
| ad 100 | Dist. water |

Preparation:
Weigh in components and dissolve. Adjust pH to 6 to 7.

The example can be repeated with the polymers of Examples 2 to 20. In each case, a clear shower gel with good properties is obtained.

We claim:

1. A copolymer prepared by free-radical polymerization of a monomer mixture M which comprises
   a) 50 to 80% by weight of ethyl methacrylate;
   b) 2 to 25% by weight of methyacrylamide, N-tert-butylacrylamide, or a mixture thereof;
   c) 15 to 35% by weight of a mixture of methacrylic acid and acrylic acid, wherein the weight ratio of methacrylic acid to acrylic acid is greater than 1; and
   d) 0 to 20% by weight of additional free-radically polymerizable monomers, with the proviso that said additional free-radically polymerizable monomers are not the monomers of a), b) and c).

2. The copolymer of claim 1, wherein the weight ratio of methacrylic acid to acrylic acid in said mixture of methacrylic acid and acrylic acid is greater than 2.

3. The copolymer of claim 1, wherein d) comprises at least one compound with a free-radically polymerizable α,β-ethylenically unsaturated double bond and at least one cationogenic and/or cationic group per molecule in copolymerized form.

4. The copolymer of claim 1, wherein d) optionally is a monomer selected from the group consisting of N-[3-(dimethylamino)propyl](meth)acrylamide, N-(tert-butyl)aminoethyl methacrylate, vinylimidazole, and mixtures thereof.

5. The copolymer of claim 1, wherein a) is 60 to 75% by weight of ethyl methacrylate; b) is 7 to 15% by weight of methyacrylamide, N-tert-butylacrylamide, or a mixture thereof; c) is 18 to 27% by weight of said mixture of methacrylic acid and acrylic acid; and d) is 0 to 15% by weight of said additional free-radically polymerizable monomers.

6. The copolymer of claim 1, wherein a) is 60 to 70% by weight of ethyl methacrylate; b) is 8 to 12% by weight of methyacrylamide, N-tert-butylacrylamide, or a mixture thereof; c) is 20 to 25% by weight of said mixture of methacrylic acid and acrylic acid; and d) is 0 to 10% by weight of said additional free-radically polymerizable monomers.

7. The copolymer of claim 4, wherein said ethyl methacrylate of a) is present in an amount of from 50 to 80% by weight; wherein b) is methacrylamide present in an amount of from 2 to 15% by weight; and wherein in said mixture of methacrylic acid and acrylic acid in c), said methacrylic acid is present in an amount of from 15 to 25% by weight and said acrylic acid is present in an amount of from 1 to 10% by weight.

8. The copolymer of claim 4, wherein said ethyl methacrylate of a) is present in an amount of from 50 to 80% by weight; wherein b) is N-(tert-butyl)acrylamide present in an amount of from 3 to 25% by weight; and wherein in said mixture of methacrylic acid and acrylic acid in c), said methacrylic acid is present in an amount of from 15 to 25% by weight and said acrylic acid is present in an amount of from 1 to 10% by weight.

9. A cosmetic or pharmaceutical composition comprising
   A) at least one copolymer of claim 1; and
   B) at least one cosmetically or pharmaceutically acceptable carrier.

10. The composition of claim 9 wherein B) is water, water-miscible organic solvents, oils, fats, waxes, esters of $C_6$-$C_{30}$-monocarboxylic acids with mono-, di- or trihydric alcohols which are different from iii), saturated acyclic and cyclic hydrocarbons, fatty acids, fatty alcohols, propellant gases, or mixtures thereof.

11. The composition of claim 9, additionally comprising at least one additive different from A) and B) and which is selected from the group consisting of cosmetically active ingredients, emulsifiers, surfactants, preservatives, perfume oils, thickeners, hair polymers, hair and skin conditioners, graft polymers, water-soluble or dispersible silicone-containing polymers, photoprotective agents, bleaches, gel formers, care agents, colorants, tinting agents, tanning agents, dyes, pigments, bodying agents, humectants, regreasing agents, collagen, protein hydrolyzates, lipids, antioxidants, antifoams, antistats, emollients, and softeners.

12. The composition of claim 9, wherein said composition is in the form of a gel, foam, spray, mousse, ointment, cream, emulsion, suspension, lotion, milk, or paste.

13. The composition of claim 9, wherein said composition has a fraction of volatile organic components equal to or less than 80% by weight.

14. A skin-cleansing composition, a composition for the care and protection of the skin, a nail care composition, a preparation for decorative cosmetics, or a hair-treatment composition comprising the copolymer of claim 1.

15. A hair-treatment composition setting agent and/or conditioner comprising the copolymer of claim 1.

16. The hair-treatment composition of claim 14, wherein said composition is in the form of a hair gel, shampoo, setting foam, hair tonic, hairspray, or hair foam.

17. A pharmaceutical auxiliary, a rheological modifier, a surface-active compound, an adhesive, or a textile, paper, printing, or leather coating comprising the copolymer of claim 1.

* * * * *